United States Patent
Hoeg-Jensen et al.

(10) Patent No.: US 7,316,999 B2
(45) Date of Patent: Jan. 8, 2008

(54) GLUCOSE DEPENDENT RELEASE OF INSULIN FROM GLUCOSE SENSING INSULIN DERIVATIVES

(75) Inventors: Thomas Hoeg-Jensen, Klampenborg (DK); Svend Havelund, Bagsvaerd (DK); Jan Markussen, Herlev (DK); Soren Ostergaard, Bronshoj (DK); Signe Ridderberg, Lyngby (DK); Per Balschmidt, Espergaerde (DK); Lauge Schaffer, Copenhagen (DK); Ib Jonassen, Valby (DK)

(73) Assignee: Novo Nordisk A/S, Bagsvaerd (DK)

( * ) Notice: Subject to any disclaimer, the term of this patent is extended or adjusted under 35 U.S.C. 154(b) by 122 days.

(21) Appl. No.: 09/870,884

(22) Filed: May 31, 2001

(65) Prior Publication Data

US 2002/0028767 A1 Mar. 7, 2002

Related U.S. Application Data

(60) Provisional application No. 60/213,375, filed on Jun. 23, 2000.

(30) Foreign Application Priority Data

Jun. 2, 2000 (DK) ................................ 2000 00858

(51) Int. Cl.
*A61K 38/28* (2006.01)
*C07K 14/62* (2006.01)
(52) U.S. Cl. ........................ 514/3; 424/426; 530/303
(58) Field of Classification Search ............... 530/303, 530/304, 305; 514/3, 4; 424/422, 423, 424, 424/425, 426
See application file for complete search history.

(56) References Cited

U.S. PATENT DOCUMENTS 5,478,575 A * 12/1995 Miyazaki et al. ........... 424/487

FOREIGN PATENT DOCUMENTS

| EP | 0 511 600 | 11/1992 |
|----|-----------|---------|
| EP | 0 368 187 | 9/1993 |
| EP | 0 254 516 | 1/1994 |
| EP | 0 712 862 | 3/1998 |
| WO | WO 84/01896 A1 * | 5/1984 |
| WO | 95/07931 | 3/1995 |
| WO | 96/00107 | 1/1996 |
| WO | 97/31022 | 8/1997 |
| WO | 98/02460 | 1/1998 |
| WO | 99/21888 | 5/1999 |
| WO | WO99/21888 A1 * | 5/1999 |

OTHER PUBLICATIONS

Brownlee et al. Glycosylated Insulin Complexed to Concanavalin A. Diabetes. vol. 32, pp. 499-504 (Jun. 1983).*
Jeong et al. Self-Regulating Insulin Delivery Systems. Journal of Controlled Release. vol. 1, pp. 57-66 (1984).*
Shiino et al. Preparation and characterization of a glucose-responsive insulin-releasing polymer device. Biomaterials. vol. 15, No. 2, pp. 121-128 (1994).*
Journal of Organic Chemistry, Eggert et al., (1999) vol. 64, pp. 3846-3852.

* cited by examiner

*Primary Examiner*—Jeffrey Edwin Russel
(74) *Attorney, Agent, or Firm*—Rosemarie R. Wilk-Oresean

(57) ABSTRACT

Insulin derivatives having a built-in glucose sensor, capable of delivering insulin from a depot as a function of the glucose concentration in the surrounding medium (e.g. tissue), such that the rate of insulin release from the depot increases with an increased glucose concentration and decreases with a decreased glucose concentration.

26 Claims, 4 Drawing Sheets

GLUCOSE DEPENDENT RELEASE OF INSULIN FROM GLUCOSE SENSING INSULIN DERIVATIVES

This application claims priority under 35 U.S.C. § 119 of U.S. Provisional Application No. 60/213,375 filed on Jun. 23, 2000, and Danish application no. PA 2000 00858, filed on Jun. 2, 2000.

FIELD OF THE INVENTION

The present invention relates to insulin derivatives having a built-in glucose sensor, capable of delivering insulin from a depot as a function of the glucose concentration in the surrounding medium (e.g. tissue).

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is partly or completely lost.

Since the discovery of insulin in the 1920's, continuous strides have been made to improve the treatment of diabetes mellitus. To help avoid extreme glycaemia levels, diabetic patients often practice multiple injection therapy, whereby insulin is administered with each meal. Many diabetic patients are treated with multiple daily insulin injections in a regimen comprising one or two daily injections of a protracted insulin composition to cover the basal requirement, supplemented by bolus injections of a rapid acting insulin to cover the meal-related requirements.

Insulin compositions having a protracted profile of action are well known in the art. Thus, one main type of such insulin compositions comprises injectable aqueous suspensions of insulin crystals or amorphous insulin. Typically, the insulin in these compositions is provided in the form of protamine insulin, zinc insulin or protamine zinc insulin.

When human or animal insulin is brought to form higher associated forms, e.g. in the presence of $Zn^{2+}$-ions, precipitation in the form of crystals or amorphous product is the result; see for example pages 20–27 in Jens Brange (editor), *Galenics of Insulin*, Springer Verlag (1987). Thus, at pH 7, addition of 6 $Zn^{2+}$ ions per insulin hexamer to a solution of porcine insulin will lead to an almost complete precipitation of the insulin.

SUMMARY OF THE INVENTION

We have invented new insulin derivatives from which the release of insulin from an injected or inhaled depot thereof is glucose dependent. In the depot, the insulin derivative modified with a glucose sensor is either in the crystalline state or in a highly aggregated soluble state. Both states bring about a protracted absorption from the site of injection. The solubility of the crystals and the state of aggregation in the soluble aggregates are influenced by the glucose concentration in the surrounding tissue. Increasing the concentration of glucose promotes dissolution of the crystals and dissociation of the soluble aggregates.

The dose and volume of the subcutaneous or intramuscularly injected depot is similar to that of the ordinary basal insulin compositions, meant to cover basal insulin supply by injection once or twice daily. Inhaled insulin compositions of insulin derivatives having glucose sensor may be taken several times during the day, typically before or during the meals.

Soluble insulin derivatives featuring lipophilic substituents, capable of forming high molecular weight aggregates having a higher molecular weight than aldolase (Mw=158 kDa), have been disclosed in WO 99/21888 (Novo Nordisk) the contents of which is hereby incorporated in its entirety by reference. The release of insulin derivative from such aggregates appears to depend upon diffusion controlled disintegration of the soluble aggregates. However, some high molecular aggregates, formed from selected insulin derivatives, disintegrate and form smaller aggregates when glucose is introduced into a buffer solution containing an aggregated insulin derivative. The higher the glucose concentration, the more thorough is the disintegration of the aggregated derivative.

The state of aggregation and the power of glucose to diminish this state can be demonstrated by gel filtration of the aggregated insulin derivatives in buffers containing varying concentrations of glucose in the eluents.

The increased release of insulin derivative from subcutaneous depots can be demonstrated by the different levels of the insulin derivative in the plasma of pigs clamped at various blood glucose levels, e.g. 5 and 10 mM, after injection of the same dose of the insulin derivative.

This new concept of glucose dependent insulin release complies with the convenience of the state of the art injection regimens of insulin therapy, and requires neither surgery nor the danger associated with storage of large implanted depots in the body.

BRIEF DESCRIPTION OF THE DRAWING

The present invention is further illustrated with reference to the appended drawing wherein.

AU IS ABSORBANCE UNITS

DETAILED DESCRIPTION OF THE INVENTION

Figure 1:
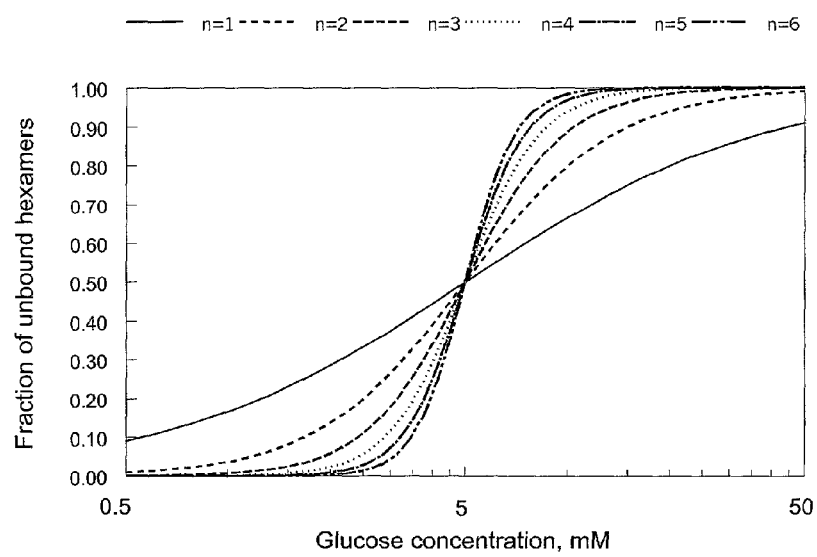
FIG. 1 shows that a steep correlation between the release of insulin and the glucose concentration is possible by the multiple interactions between insulin hexamers as compared to a mechanism involving just one bond.

The expression "insulin derivative" as used herein (and related expressions) refers to human insulin or an analogue thereof in which at least one organic substituent is bound to one or more of the amino acids.

By "analogue of human insulin" as used herein (and related expressions) is meant human insulin in which one or more amino acid residues have been deleted and/or replaced by other amino acid residues, including non-codeable amino acid residues, or human insulin comprising additional amino acid residues, i.e. more than 51 in total. The amino acid sequence of human insulin is given i.a. in The Merck Index, 11th Edition, published in 1989 by Merck & Co., Inc., page 4888. The sequence of human insulin, A and B chains, is as follows: Human insulin, A chain: G-I-V-E-Q-C-C-T-S-I-C-S-L-Y-Q-L-E-N-Y-C-N (SEQ ID NO: 1); Human insulin, B chain: F-V-N-Q-H-L-C-G-S-H-L-V-E-A-L-Y-L-V-C-G-E-R-G-F-F-Y-T-P-K-T (SEQ ID NO: 2). Analogs of human insulin exemplified in the instant invention include, but are not limited to the following: Human insulin, Asp$^{B28}$ chain analog: F-V-N-Q-H-L-C-G-S-H-L-V-E-A-L-Y-L-V-C-G-E-R-G-F-F-Y-T-D-K-T (SEQ ID NO: 3); Human insulin, Lys$^{B28}$, Pro$^{B29}$ B chain analog: F-V-N-Q-H-L-C-G-S-H-L-V-E-A-L-Y-L-V-C-G-E-R-G-F-F-Y-T-K-P-T (SEQ ID NO: 4); Human insulin, Gly$^{A21}$ A chain analog: G-I-V-E-Q-C-C-T-S-I-C-S-L-Y-Q-L-E-N-Y-C-G (SEQ ID NO: 5); Human insulin, Lys$^{B3}$, Ile$^{B28}$ B chain analog: F-V-K-Q-H-L-C-G-S-H-L-V-E-A-L-Y-L-V-C-G-E-R-G-F-F-Y-T-I-K-T (SEQ ID NO: 6); Human insulin, Asp$^{A21}$ A chain analog: G-I-V-E-Q-C-C-T-S-I-C-S-L-Y-Q-L-E-N-Y-C-D (SEQ ID NO: 7); Human insulin, des$^{B30}$ B chain analog: F-V-N-Q-H-L-C-G-S-H-L-V-E-A-L-Y-L-V-C-G-E-R-G-F-F-Y-T-P-K (SEQ ID NO: 8); Human insulin, Phe$^{B26}$ B chain analog: F-V-N-Q-H-L-C-G-S-H-L-V-E-A-L-Y-L-V-C-G-E-R-G-F-F-F-T-P-K-T (SEQ ID NO: 9); Human insulin, Orn$^{B30}$ B chain analog: F-V-N-Q-H-L-C-G-S-H-L-V-E-A-L-Y-L-V-C-G-E-R-G-F-F-Y-T-P-K-X (SEQ ID NO: 10)

X=ornithine; Human insulin, Dap$^{B30}$ B chain analog: F-V-N-Q-H-L-C-G-S-H-L-V-E-A-L-Y-L-V-C-G-E-R-G-F-F-Y-T-P-K-X (SEQ ID NO: 11)

X=diaminopropionic acid; Human insulin, Lys$^{B30}$ B chain analog: F-V-N-Q-H-L-C-G-S-H-L-V-E-A-L-Y-L-V-C-G-E-R-G-F-F-Y-T-P-K-K (SEQ ID NO: 12); Human insulin, Pro$^{B30}$ B chain analog: P-F-V-N-Q-H-L-C-G-S-H-L-V-E-A-L-Y-L-V-C-G-E-R-G-F-F-Y-T-P-K-T (SEQ ID NO: 13); Human insulin, Asp$^{B30}$ B chain analog: F-V-N-Q-H-L-C-G-S-H-L-V-E-A-L-Y-L-V-C-G-E-R-G-F-F-Y-T-P-K-D (SEQ ID NO: 14); Human insulin, Glu$^{B30}$ B chain analog: F-V-N-Q-H-L-C-G-S-H-L-V-E-A-L-Y-L-V-C-G-E-R-G-F-F-Y-T-P-K-E (SEQ ID NO: 15); Human insulin, Ams(BOC)$^{B30}$ B chain analog: F-V-N-Q-H-L-C-G-S-H-L-V-E-A-L-Y-L-V-C-G-E-R-G-F-F-Y-T-P-K-X (SEQ ID NO: 16)

X=O-aminoserine(BOC); and Human insulin, Dab$^{B30}$ B chain analog: F-V-N-Q-H-L-C-G-S-H-L-V-E-A-L-Y-L-V-C-G-E-R-G-F-F-Y-T-P-K-X (SEQ ID NO: 17)

X=diaminobutyric acid.

By "depot" is meant the amount of subcutaneous or intramuscularly injected or inhaled insulin composition, either in the form of crystalline compositions, such as NPH insulin and Lente insulin, or as solutions, such as albumin binding or soluble aggregating or acid solutions of neutral-precipitating, of insulin analogues or insulin derivatives.

By "absorption" is meant the process by which the insulin in the depot is transferred to the circulation.

By "glucose sensor" is meant a chemical group, capable of binding to or reacting with glucose. The glucose sensor is part of the insulin molecule. For reversible binding, the dissociation constant, $K_d$, of the sensor-glucose complex is usually in the range from 0.01 µM to 100 mM, for example from 1 µM to 20 mM or from 1 mM to 20 mM or from 1 mM to 100 mM. Examples of reversible glucose sensors are organic borates, preferably aryl boronates or other borates, where the attachment to an insulin derivative is via a carbon-boron bond. Alkyl boronates are oxidatively labile and often unstable (Snyder, Kuck and Johnson, J. Am. Chem. Soc 1938, 60, 105). Boronate sensors that bind glucose under physiological conditions are preferred. Simple aryl boronates, such as phenyl boronate, binds glucose only at relatively high pH, >9 (Shinkai and Takeuchi, Trends Anal. Chem. 1996, 15, 188). Acidic boronates, which bind glucose at physiological pH, are preferred. Examples of such boronate glucose sensors are aminomethyl-aryl-2-boronates (Bielecki, Eggert and Norrild, J. Chem. Soc., Perkin Trans 2 1999, 449), other boronates with amino groups in the vicinity (Shiino et al, J. Controlled Release 1995, 37, 269), or aryl boronates substituted with electron-withdrawing groups (Eggert et al., J. Org. Chem. 1999, 64, 3846), e.g. sulfo-, carboxy-, nitro-, cyano-, fluoro-phenyl boronates, pyridine boronates, pyridinium boronates or their combinations. Diboronates may be employed to insure glucose-selectivity over for instance fructose.

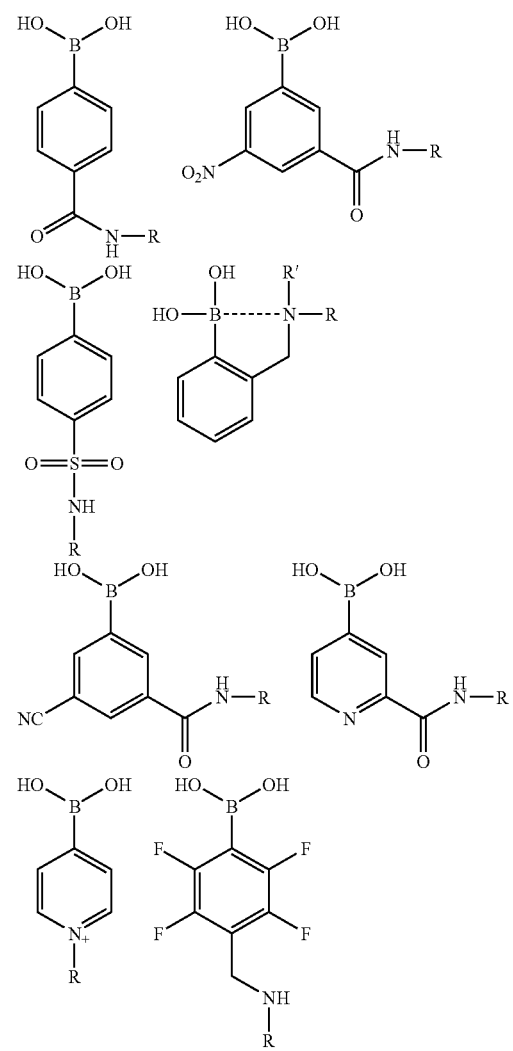

Such acidic boronates assume a tetrahedral configuration in aqueous solvent at physiological pH, thereby allowing binding of glucose. Reversible glucose sensors may also be peptides or pseudopeptides, optionally containing boronates. Examples of irreversible glucose binders are oxyamines and hydrazines, which react with glucose to form oximes and hydrazones (Veprek and Jezek, J. Peptide Sci. 1999, 5, 203; Peri, Dumy and Mutter, Tetrahedron 1998, 54, 12269). Examples of useful oxyamine functions are aminoxyacetic acid, AOA (Vilaseca et al. Bioconjugate Chem. 1993, 4, 515), and O-aminoserine, Ams (Spetzler and Hoeg-Jensen, J. Pept. Sci. 1999, 5, 582).

In theory, one way to obtain tight glucose control would be to couple a glucose sensor, positioned in the tissue of the patient, to a computer that controls an insulin pump. The pump is via a catheter connected to a needle inserted under the skin. However, it appears as if such a feed back control system has not yet been implemented, possibly because of lack of stable and reliable of glucose sensors. Glucose sensors inserted in the tissue appears to get overgrown with fibrin, and it appears that non-invasive sensors, e.g. based on infrared optics, remain to be invented or developed.

Attempts to develop systems for glucose dependent release of insulin from a depot has previously been described. A carbohydrate binding lectin, such as concanavalin A, immobilized to a solid matrix, such as hollow fibres, binds an insulin derivative substituted with a carbohydrate moiety, such as maltotriose, maltose or dextran. The matrix allows diffusion of dissolved glucose and insulin derivative. As the systemic glucose concentration rises, glucose displaces increasing amounts of the insulin derivative from the matrix, thus making more insulin available to the circulation, and thereby to the insulin receptors, when it is needed. It appears as if none of these lectin based systems have been implemented clinically, probably due to the inconvenience of implanting the insulin containing matrix in the body, and to the danger of carrying a large insulin depot within the body.

Another suggested glucose-controlled insulin release system is based on the glucose oxidase catalysed conversion of glucose to gluconic acid. The glucose oxidase is immobilized to a matrix, e.g. of ethylene/vinyl acetate copolymer, and the insulin or insulin derivative is trapped in the matrix in the solid state. As the pH is lowered locally due to the production of gluconic acid the solubility of insulin increases. Thus, the rate of release of soluble insulin from the solid state reflects the glucose concentration. Likewise, it appears as if none of these glucose oxidase based systems have been implemented clinically, possibly for the same reasons.

Furthermore, attempts to provide glucose controlled insulin release from a depot in which the glucose sensing molecular structure is part of a matrix, i.e. a soluble or solid polymer have been made.

Another type of protracted insulin compositions is a solution having a pH value below physiological pH from which the insulin analogue will precipitate when the solution is injected because of the rise in the pH value to physiological pH when the solution has been injected. This principle may be combined with the present invention by incorporation of the glucose-sensor in the insulin analogue. In addition to the glucose sensor these analogues have an amino acid residue in position A21 which is stable at pH values as low as practically useful in solutions to be injected. Examples of suitable amino acid residues at position A21 are glycine, serine and alanine. Also, the insulins have mutations to increase the net charge of the molecule by about 2 units, e.g. Thr in position B27 can be substituted with Arg and Thr-OH in position B30 can be substituted with Thr-$NH_2$ or basic residues can be added, e.g. B31–B32 Arg-Arg.

Soluble insulin derivatives having a lipophilic substituent linked to the ε-amino group of a lysine residue in any of the positions B26 to B30 have been described in the literature. Such derivatives have a protracted profile of action after subcutaneous injection as compared to soluble human insulin, and this protracted action has been explained by a reversible binding to albumin in subcutis, blood and peripheral tissue.

An additional mechanism of prolonging the action of some of the soluble insulin derivatives featuring a lipophilic substituent has been disclosed, i.e. derivatives capable of forming high molecular weight aggregates, having a higher molecular weight than aldolase (Mw=158 kDa) when analysed in a defined gel filtration system.

In healthy persons, the blood glucose concentration is about 5 mM, rising to about 7 mM after the meals. Today, even when applying the most advanced insulin treatment, using rapid acting insulins for meal-related injections and soluble depot insulin for basal insulin based on frequent monitoring of blood glucose, diabetics often experience glucose concentrations out of control. If too much insulin is administered, so that glucose concentrations get below about 3 mM, hypoglycaemic events might occur, leading to unconsciousness. When too little insulin is administered and glucose concentrations rises to about 20 mM, acetone appears in the blood and gives rise to diabetic ketoacidosis and, eventually, diabetic coma. However, it is desirable to control the blood glucose concentration of diabetics more tightly, as close to the 5 mM as possible, in order to diminish diabetic late complications. The DCCT (Diabetes Complication Clinical Trial) study from 1993 in USA examined the development of diabetic complications in type 1 diabetics during 9 years (N Engl J Med 1993, 329, 977–986). The UKPDS (United Kingdom Prospective Diabetes Study) studied the development of complications in type 2 diabetics during 15 years (Lancet 1998, 352, 854–865). Even though the pattern of complications differs between these two types of diabetics both investigations conclude that a tight control of blood glucose results in a marked reduction of complications. Thus, there is an unmet medical need for means to obtain glucose control in diabetics closer to the normal value of 5 mM.

In one preferred embodiment the present invention is based on the discovery of soluble and aggregated forms of insulin derivatives, wherein the state of aggregation is being influenced by glucose. The aggregate is preferably soluble in water at neutral pH, in the range of 6.8 to 8.5. The soluble, aggregated forms of insulin derivatives dissociates slowly after subcutaneous injection, making them suitable for a long-acting insulin composition, the advantage being that the composition contains no precipitate. The higher the concentration of glucose is in the tissue the higher the rate of dissociation and of the subsequent absorption. The advantages of soluble rather than suspended compositions are higher precision in dosing, avoidance of shaking of the vial or pen, allowance for a thinner needle meaning less pain during injection, easier filling of vials or cartridge and avoidance of a ball in the cartridge used to suspend the precipitate in the absence of air.

The apparent volume of elution of aggregates, as estimated by the distribution coefficient, $K_{AV}$, changes to a higher value when the glucose concentration is increased from 0 to 20 mM or to 100 mM, as determined by gel filtration using a Bio-Gel P300 (BIO-RAD). In order to achieve an optimal effect of glucose on the state of aggregation in this experiment, the concentration of sodium chloride should be decreased just to obtain an aggregation about the size of aldolase (i.e. the $K_{AV}$ value of 0.10).

The aggregated form can be observed for insulin derivatives under conditions where the hexameric unit is known to exist for most insulins. Thus, in a preferred embodiment, the aggregated form is composed of hexameric subunits, preferably of at least 4, more preferably 5 to 500, hexameric subunits. Any hexameric subunit of the aggregated forms of the compounds of this invention may have any of the known $R_6$, $R_3T_3$, or $T_6$ structures, $T_6$ being the preferred form (Kaarsholm, Biochemistry 28, 4427–4435, 1989).

Substances like $Zn^{2+}$ known to stabilise the hexameric unit are also found to stabilise the aggregated form of some insulin derivatives. The building blocks forming the aggregates may be the hexameric units known from the X-ray crystallographic determined structure of insulin (Blundell, Diabetes 21 (Suppl. 2), 492–505, 1972). Ions like $Zn^{2+}$, known to stabilise the hexameric unit as 2 or 4 $Zn^{2+}$/hexamer complexes (Blundell, Diabetes 21 (Suppl. 2), 492–505, 1972), are essential for the formation of aggregates for most insulin analogues and derivatives. Thus, compositions of glucose dependent aggregating insulin derivatives according to this invention preferably comprises at least 2 zinc ions, more preferably 2 to 5 zinc ions, still more preferably 2 to 3 zinc ions, per 6 molecules of insulin derivative. Moreover, the compositions advantageously comprise at least 3 molecules of a phenolic compound per 6 molecules of insulin derivative. In the central cavity of the 2 $Zn^{2+}$/hexamer structure 6 residues of $Glu^{B13}$ provide binding sites for up to 3 $Ca^{2+}$ ions (Sudmeier et al., Science 212, 560–562, 1981). Thus, addition of $Ca^{2+}$ ions stabilises the hexamer and may be added to the pharmaceutical compositions, on the condition that the insulin derivative remains in solution.

The disappearance half-time of the aggregate of the invention after subcutaneous injection in healthy human subjects, having normal blood glucose concentrations about 5 mM, is preferably as long as or longer than that of a human insulin NPH composition.

In a particularly preferred embodiment of the present invention, the aggregate is composed of insulin derivatives, which have an albumin binding which is lower than that of $Lys^{B29}(N^{\epsilon}$-tetradecanoyl) des(B30) human insulin.

The substituent at the lysine residue of the insulin derivative of the aggregate according to the invention is preferably a lipophilic group containing from 6 to 40 carbon atoms.

Examples of suitable lipophilic substituents (groups) are the acid residues of lithocholic acid, cholic acid, hyocholic acid, deoxycholic acid, chenodeoxycholic acid, ursodeoxycholic acid, hyodeoxycholic acid or cholanic acid.

In another preferred embodiment, the lipophilic substituent is connected to the $\epsilon$-amino group of a lysine residue using an amino acid linker. According to this embodiment the lipophilic substituent is advantageously connected to a lysine residue via a γ- or an α-glutamyl linker or via a β- or an α-aspartyl linker.

In yet another preferred embodiment the lipophilic substituent comprises the glucose sensor in the form of a borate group, an aryl boronate, an amino aryl boronate or a glucose binding peptide.

The present invention furthermore provides novel insulin derivatives capable of forming aggregates, in which the degree of aggregation is inversely correlated to the glucose concentration. These insulin derivatives may be provided in the form of aggregates in pharmaceutical compositions or, alternatively, they may be provided in a non-aggregated form in pharmaceutical compositions, in which case the aggregates form after subcutaneous injection of said compositions.

Accordingly, the present invention furthermore is concerned with pharmaceutical compositions comprising an aggregate of insulin derivatives or non-aggregated insulin derivatives, which form aggregates after subcutaneous injection, the degree of aggregation being inversely correlated to the glucose concentration. The dissociation of the soluble insulin polymers into soluble insulin hexamers by the action of glucose molecules can be described by the following equation:

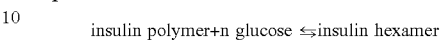

where n is the number of glucose molecules required to break the polymeric insulin network, releasing the insulin hexamers from the network. The advantage of n being larger than 1 is apparent from FIG. 1, which shows that increasing n from 1 to 6 increases the steepness of the curve for the fraction of free insulin hexamers over polymer, bound insulin hexamers. Thus, a faster release of insulin at a high glucose concentration, and a slower release at a low glucose concentration, is possible by the multiple interactions between insulin hexamers than by a mechanism involving just one bond.

Preferably, the pharmaceutical composition according to the present invention comprises aggregates, a substantial fraction of which have a higher molecular weight than aldolase as determined by gel filtration using the medium of the composition as eluent.

In another embodiment, a pharmaceutical composition comprises both aggregating and rapid acting insulin analogues, the latter preferably being human insulin or one of the insulin analogues $Asp^{B28}$ human insulin, $Lys^{B28}Pro^{B29}$ human insulin, $Gly^{A21}, Lys^{B3}, Ile^{B28}$ human insulin, $Asp^{A21}$, $Lys^{B3}, Ile^{B28}$ human insulin or des(B30) human insulin. Such a composition will provide both a rapid onset of action and a prolonged profile of action, the latter being influenced by the blood glucose concentration of the diabetic patient. In case the two insulins of the mixture form mixed hexamers both will be under influence of the blood glucose concentration.

In this embodiment, the pharmaceutical composition preferably comprises aggregating insulin and rapid acting insulin in a molar ratio of from 90:10 to 10:90.

The slow dissociation of the aggregated forms may be further slowed down in vivo by the addition of physiological acceptable agents that increase the viscosity of the pharmaceutical composition. Thus, the pharmaceutical composition according to the invention may furthermore comprise an agent that increases the viscosity, preferably polyethylene glycol, polypropylene glycol, copolymers thereof, dextrans and/or polylactides.

In yet another embodiment, the insulin derivative containing a glucose sensing group is prepared as a crystalline NPH composition, using protamine to form the crystals, or as a crystalline Lente composition, using $Zn^{2+}$-ions in the crystals. In these cases the rate of dissolution of the crystals is enhanced by the interaction between glucose and the glucose sensing group.

In yet another embodiment, the protracted insulin compositions are solutions having a pH value below physiological pH from which the insulin analogue will precipitate because of the rise in the pH value to physiological pH when the solution has been injected. Such analogues are described in EP 0 254 516 B1 (Novo Nordisk) and EP 0 368 187 B1 (Hoechst). These analogues have an amino acid residue in position A21 which is stable at pH values as low as practically useful in solutions to be injected. Examples of suitable amino acid residues at position A21 are glycine, serine or alanine. Also, the insulins have mutations to increase the net charge of the molecule by about 2, e.g. Thr in position B27 can be substituted with Arg and Thr-OH in position B30 can be substituted with Thr-NH$_2$ or have additional basic residues, e.g. B31–B32 Arg-Arg. When this principle is combined with the present invention by incorporation of the glucose-sensor in these insulin analogues, the solubility of the crystals is enhanced by the interaction between glucose and the glucose sensing group, facilitating the absorption.

Sites enabling the attachment of a glucose sensor are the N-terminal amino groups of glycine A1 and phenylalanine B1 and the ε-amino group of lysine B29. One or more additional or alternative lysine residues may be incorporated for this purpose, e.g. in position B3 or B28. Furthermore the glucose sensor may be incorporated as part of the peptide chain, preferably in the C-terminal part of the B-chain.

The pharmaceutical composition preferably further comprises a buffer substance, such as a phosphate, for example sodium phosphate, glycine or glycylglycine buffer, an isotonicity agent, such as sodium chloride or glycerol, and phenol and/or m-cresol as a preservative. Optionally, mannitol or sorbitol can be added as isotonicity agents and the resulting interaction with the glucose sensor can be utilized to adjust stability and the release profile of the composition. Among the auxiliary substances of a pharmaceutical composition according to the present invention, the sodium chloride, used as isotonic agent, the zinc- and optionally calcium ions, which promote and stabilize the hexamer formation, are particularly important since they facilitate the aggregation of the insulin derivative in the composition and thereby effectively prolong the time of disappearance from the site of injection. A pharmaceutical composition according to the invention preferably comprises chloride ions in a concentration of 5 to 150 mM.

In pharmaceutical compositions, the concentration of the glucose-sensing insulins of the present invention is generally in the range from 0.1 to 15 mM for example from 0.1 to 2 mM. The amount of zinc contained in the compositions is 0.3–0.9% by weight relative to the insulin derivative. Phenolic compounds like phenol or m-cresol or mixtures thereof are suitably applied in a total concentration of from 5 to 50 mM, and chloride ions in a concentration of from 10 mM to 100 mM.

The present invention furthermore relates to a method of treating diabetes mellitus comprising administering to a person in need of such treatment an effective amount of water-soluble aggregates of insulin derivatives according to the invention or effective amount an insulin derivative according to the invention, capable of forming water-soluble aggregates upon subcutaneous injection, aggregate size depending on the glucose concentration.

The optimal dose level for any patient will depend on a variety of factors including the efficacy of the specific human insulin derivative employed, the age, body weight, physical activity, and diet of the patient, on a possible combination with other drugs, and on the severity of the case of diabetes. It is recommended that the daily-dosage of the human insulin derivative of this invention be determined for each individual patient by those skilled in the art in a similar way as for known insulin compositions.

The glucose sensor building blocks used in preparation of the glucose-sensing insulins can be prepared as described in the included examples. The insulin derivatives of the invention can be prepared by the general methods disclosed in WO 95/07931 (Novo Nordisk A/S), WO 96/00107 (Novo Nordisk A/S), WO 97/31022 (Novo Nordisk A/S), WO 98/02460 (Novo Nordisk A/S), EP 511 600 (Kuraray Co. Ltd.) and EP 712 862 (Eli Lilly).

Some of the derivatives listed in the aforementioned patent applications, and described in the publications of Markussen, Diabetologia 39, 281–288, 1996; Kurzhals, Biochem J. 312, 725–731, 1995; Kurzhals, J. Pharm Sciences 85, 304–308, 1996; and Whittingham, Biochemistry 36, 2826–2831, 1997 as being protracted due to the albumin binding mechanism, do also posses the ability to form high molecular weight soluble aggregates. Lys$^{B29}$ (N$^\epsilon$-lithocholyl-γ-glutamyl) des(B30) human insulin from WO 95/07931 and Lys$^{B29}$(N$^\epsilon$ ω-carboxyheptadecanoyl) des (B30) human insulin from WO 97/31022 are examples of insulin derivatives capable of forming high molecular weight soluble aggregates at neutral pH.

Determination of Carbohydrate Binding

The affinity of a glucose-sensing insulin derivative towards glucose and other carbohydrates can be evaluated by experiments performed on a Biacore® sensor chip (see, for example, www.biacore.com and Rich R L; Myszka D G, *Journal of Molecular Recognition*, 13 (6) 388–407 (2000)). Biacore instruments are based on surface plasmon resonance (SPR) which is an optical technique that measures the mass of a substance bound to a dextran covered gold surface in a micro flow cell. The dextran can be chemically modified by immobilization of small molecules, peptides, or proteins. The binding of the compound to be tested to the dextran or modified dextran is measured in real time which allows kinetic measurements.

Figure 2:
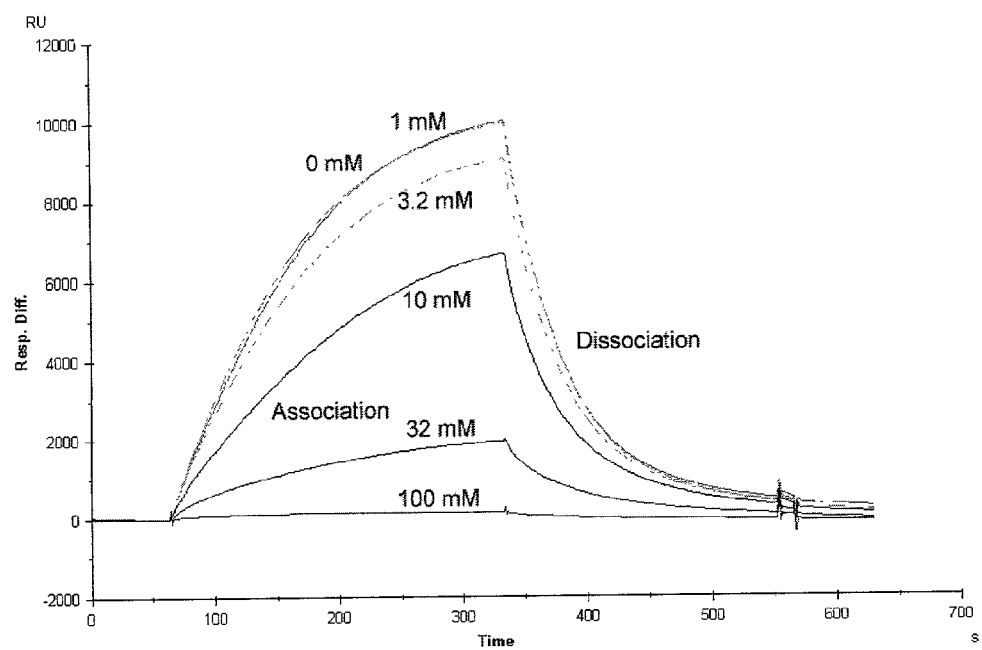
FIG. 2 shows the association and dissociation of glucose-binding insulin derivative 17a on a Biacore® glucamine sensor chip. RU is Response Units.
Figure 3:
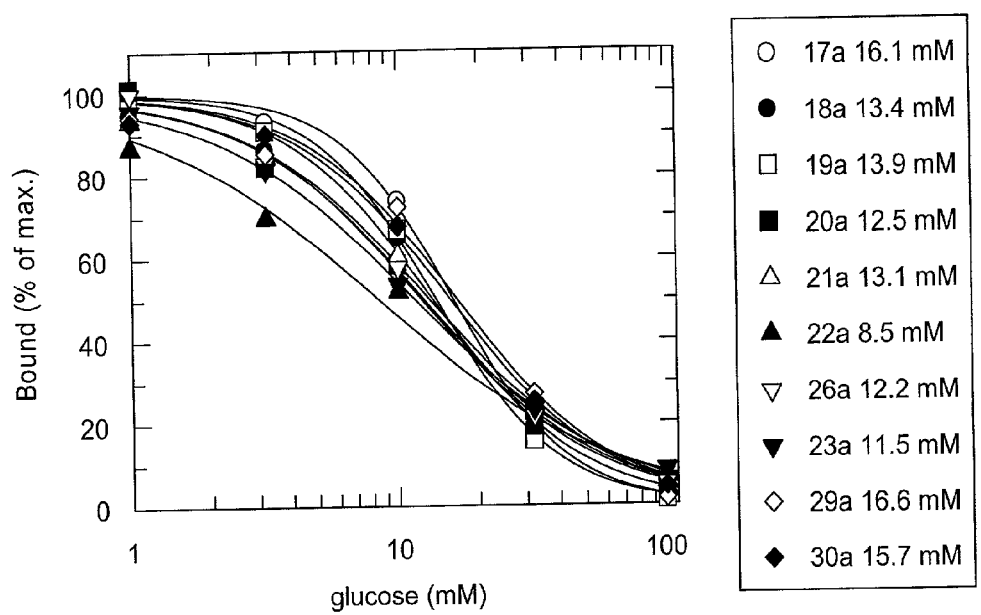
FIG. 3 shows the glucose displacement curves of a number of glucose-sensing insulin derivatives according to the invention from a Biacore® glucamine sensor chip.
Figure 4:
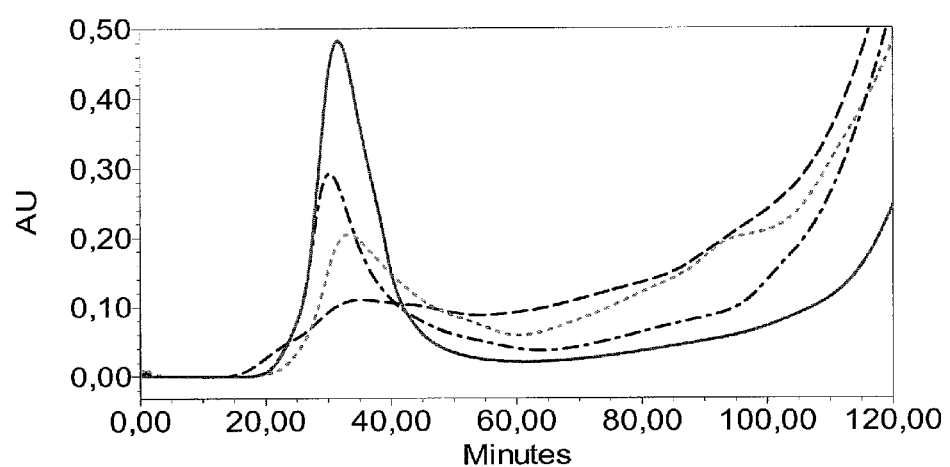
FIG. 4 shows results from the aggregation test of $Lys^{B29}$ ($N^\epsilon$-(γ-glutamyl-$N^\alpha$-lithocholoyl)-$Dap^{B30}$($N^\epsilon$-3-nitro-5-boronobenzoyl) human insulin (the title compound of Example 19), in a gel filtration assay on Bio-Gel P300 eluted at 37° C. by a) sodium chloride 100 mM, sodium phosphate 5 mM, preserved with sodium azide 0.01% and hydrochloric acid added to pH 7.4 (solid line), b) sodium chloride 25 mM, sodium phosphate 5 mM, preserved with sodium azide 0.01% and hydrochloric acid added to pH 8.0 (dash dot line), c) sodium chloride 25 mM, sodium phosphate 5 mM, preserved with sodium azide 0.01%, hydrochloric acid added to pH 8.0 and glucose 20 mM added (dot line) and d) sodium chloride 25 mM, sodium phosphate 5 mM, preserved with sodium azide 0.01%, hydrochloric acid added to pH 8.0 and glucose 200 mM added (dash line).

For the present purpose, glucamine is immobilized on a carboxylate surface by a standard amine coupling method. The glucamine-modified surface binds the glucose-sensing insulin 17a as illustrated in FIG. 2. By adding varying amounts of glucose to the 17a solution prior to pumping it over the glucamine surface it can be demonstrated that the signal diminishes when the glucose concentration is increased. The response can be quantified and plotted as a competition curve from which the EC50 can be determined, see FIG. 3. Under the conditions used (low binding), EC50 is a good estimate of the value of the dissociation coefficient, Kd. Data obtained with a number of the insulin derivatives of the present invention are presented in Table 1. The experimental conditions used in the above experiments are 0.1 M NaCl, 0.1 M phosphate, pH 7.4, 25° C.

TABLE 1

| Compound No. | EC50 (mM) |
|---|---|
| 17a | 16.1 |
| 18a | 13.4 |
| 19a | 13.9 |
| 20a | 12.5 |
| 21a | 13.1 |
| 22a | 8.5 |
| 23a | 11.5 |
| 26a | 12.2 |
| 29a | 16.6 |
| 30a | 15.7 |

Determination of Insulin Receptor Binding

The insulin activity of the insulin derivatives of the invention can be demonstrated by their binding to an insulin receptor preparation. Scintiplates (Wallac) are coated with Goat antimouse IgG and an insulin receptor antibody is added, followed by solubilized human insulin receptor. The binding of the insulins of the invention to the insulin receptor is measured by competition with $^{125}$I-TyrA14 human insulin and scintillation counting. Results obtained with insulin derivatives according to the invention are presented in Table 2.

TABLE 2

| Compound No. | EC50 (Insulin receptor) (nM) |
|---|---|
| Human insulin | 0.16 |
| 17 | 0.57 |
| 18 | 0.55 |
| 19 | 0.42 |
| 21 | 1.0 |
| 22 | 1.1 |
| 23 | 0.73 |
| 29 | 0.56 |
| 32 | 1.4 |

Determination of Aggregate Formation

The aggregated form of the insulins of the invention is demonstrated by gel filtration suing a gel with an exclusion limit higher than or equal to aldolase. An aqueous buffer system at neutral pH is used in the gel filtration and the insulin derivatives are applied to the column in the form of a pharmaceutical composition at a concentration of 600 nmol insulin/ml. Insulin derivatives in the aggregated state elute together with or before aldolase, which has a higher molecular weight of 158 kDa.

The elution volume of a gel filtration can be described by the distribution coefficient, $K_{AV}$ defined as $$K_{AV} = (V_R - V_0)/(V_t - V_0)$$

where $V_R$ is retention volume, $V_0$ is void volume and $V_t$ the total volume of the bed. $V_0$ is obtained as the elution volume of blue dextran and $V_t$ by measuring the column dimensions and calculation of the volume.

The gel filtration experiment using the conditions prescribed in this section is a direct physicochemical method which can be used to demonstrate the aggregate forming properties of the insulin derivatives of the present invention. The rate at which an insulin derivative disappears from the injection site after subcutaneous injection reflects the combined influence of the polymer formation, the glucose concentration and the albumin binding properties of the insulin derivative, besides a variety of biological factors. A convenient measure of the disappearance rate is the disappearance half life, $T_{50\%}$, which can be measured e.g. in pigs. $T_{50\%}$ is the time when 50% of the A14 Tyr($^{125}$I) analogue has disappeared from the site of injection as measured with an external γ-counter (Ribel, U et al., The Pig as a Model for Subcutaneous Absorption in Man. In: M. serrano-Rios and P. J. Lefebre (Eds): Diabetes 1985; Proceedings of the 12th Congress of the International Diabetes Federation, Madrid, Spain, 1985 (Excerpta Medica, Amsterdam, (1986) 891–96).

The formation of glucose-dependent, high molecular weight soluble aggregates may be demonstrated by gel filtration using a column of the polyacrylamide gel Bio-Gel P300 (BIO-RAD) in a neutral aqueous eluent comprising from 20 to 140 mM sodium chloride, 5 mM sodium phosphate at pH 7.4 or higher and a glucose concentration varying from 0 to 20 mM or higher, e.g. from 0 to 100 mM. For insulin derivatives eluting partly after the column volume the gel filtration may be performed with a lower sodium chloride concentration. The buffer system described was chosen to mimic the conditions in mamalian tissue in vivo, in order to be able to detect derivatives changing their state of aggregation under conditions similar to those after the subcutaneous injection. In other buffer systems, decreasing the concentration of sodium chloride, or increasing the pH value precisely to obtain aggregates having a molecular weight close to the molecular weight of aldolase, the possibility of observing glucose influence is better.

Gel filtration assay for aggregation: An empty column HR 10/10 (Amersham Pharmacia Biotech code 19-7402-01) useable for 10×1 cm column and with low dead volume was packed with Bio-Gel P-300 (BIO-RAD) according to the instruction manual (BIO-RAD) and eluted at a linear flow of 4.5 cm/h (0.06 ml/min) at 37° C. The actual column length of about 10 cm was measured to calculate the total bed volume. A 7.9 ml gel filtration column useable for separation of a wide molecular weight range, Bio-Gel 300 (BIORAD), was eluted at 37° C. by sodium chloride 100 mM, sodium phosphate 5 mM, preserved with sodium azide 0.01% and hydrochloric acid added to pH 7.4. Run time was 240 min and injection volume was 100 μl. For insulin derivatives eluting partly after the column volume the gel filtration was repeated with a lower sodium chloride concentration. The dissociation effect of glucose on the state of aggregation was tested by inclusion of glucose 20 mM or higher and optionally increasing the pH to 8.0. Data obtained with a number of the insulin derivatives of the present invention are presented in Table 3:

TABLE 3

| Compound No. | Gel filtration assay ($K_{AV}$) |
|---|---|
| Aldolase | 0.10 |
| 17 | 0.02 |
| 18 | 0.00 |
| 19 | 0.01 |
| 21 | 0.02 |
| 22 | 0.03 |
| 29 | 0.06 |
| 30 | 0.01 |
| 31 | 0.01 |
| 32 | 0.04 |

Alternative methods to study the state of aggregation are light scattering, osmometry and ultracentrifugation.

EXAMPLES

Acronyms used for chemical groups and commercially available chemicals:

| Ams | O-aminoserine |
|---|---|
| AOA | Aminooxyacetic acid |
| Boc | tert-Butoxycarbonyl |
| Bzl | Benzyl |
| Dab | Diaminobutyric acid |
| Dap | Diaminopropionic acid |
| DCC | N,N'-Dicyclohexylcarbodiimide |
| DMF | N,N-Dimethylformamide |
| Fmoc | 9-Fluorenylmethoxycarbonyl |
| HOSu | N-hydroxysuccinimide |
| NMP | N-Methyl-2-pyrrolidone |
| Orn | Ornithine |
| TEA | Triethanolamine |
| TFA | Trifluoroacetic acid |
| THF | Tetrahydrofuran |

Abbreviations:

ESMS: Electro Spray Mass Spectrometry.

HPLC: High Performance Liquid Chromatography.

LCMS: Liquid Chromatography Mass Spectrometry.

MALDI-MS: Matrix Assisted Laser Desorption Ionisation Mass Spectrometry.

Mw: Molecular weight.

Example 1

Lys$^{B29}$(N$^\epsilon$-lithocholoyl)-N-phenyl-B29-benzylamide-2-boronic acid des(B30) human insulin, 1

2,2-Dimethylpropane-1,3-diyl-2-(bromomethyl)phenylboronate (Bielecki, Eggert and Norrild, J. Chem. Soc. Perkin Trans 2, 1999, 449) was reacted with aniline to give N-phenyl-benzylamine-2-(2,2-dimethylpropane-1,3-diyl)boronate. This amine was coupled to the carboxylic acid group of LysB29 in des(B30) human insulin using achromobacter lyticus protease (Morihara and Ueno, Biotech. Bioeng. 1991, 37, 693). Subsequently, the ε-amino group of LysB29 was acylated selectively using N-hydroxysuccinimidyl lithocholate (U.S. Pat. No. 5,646,242) to give structure 1.

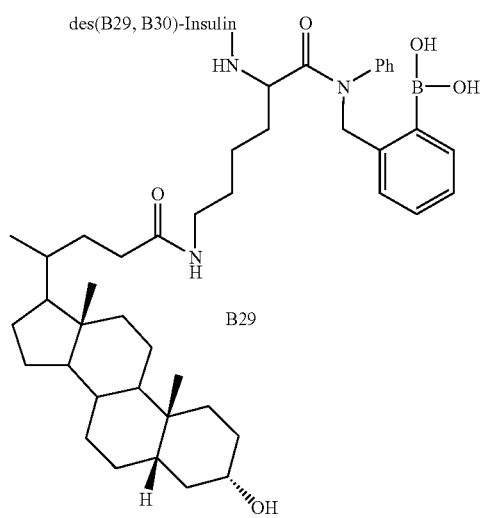

1

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 2

Lys$^{B29}$(N$^\epsilon$-lithocholoyl)-N'-methyl-N'-(benzyl-2-boronic acid)-2-amino-N-phenyl-B29-ethylamide des(B30) human insulin, 2

2,2-Dimethylpropane-1,3-diyl-2-(bromomethyl)phenylboronate (Bielecki, Eggert and Norrild, J. Chem. Soc. Perkin Trans 2, 1999, 449) was reacted with N'-phenyl-N-methylethylendiamine to give N'-phenyl-N-methyl-N-benzyl-2-(2,2-dimethylpropane-1,3-diyl)boronate ethylenediamine. This amine was coupled to the carboxylic acid group of LysB29 in des(B30) human insulin using achromobacter lyticus protease (Morihara and Ueno, Biotech. Bioeng. 1991, 37, 693). Subsequently, the ε-amino group of LysB29 was acylated selectively using N-hydroxysuccinimidyl lithocholate (U.S. Pat. No. 5,646,242) to give structure 2.

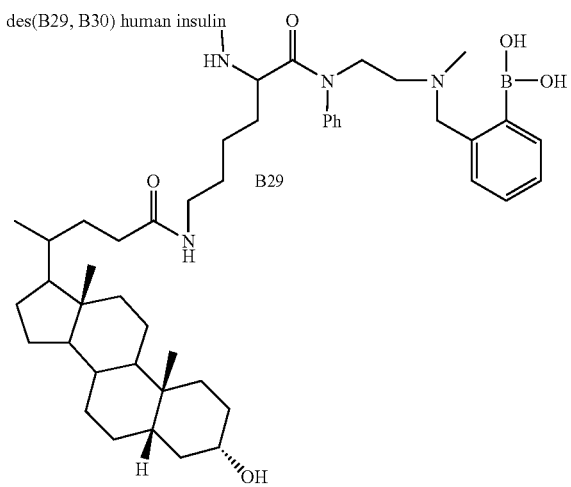

2

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 3

Lys$^{B29}$(N$^\epsilon$-lithocholoyl)-N-phenyl-B30-(benzylamide-2-boronic acid) human insulin, 3

2,2-Dimethylpropane-1,3-diyl-2-(bromomethyl)phenylboronate (Bielecki, Eggert and Norrild, J. Chem. Soc. Perkin Trans 2, 1999, 449) was reacted with methylamine to give N-methyl-benzylamine-2-(2,2-dimethylpropane-1,3-diyl) boronate. This amine was coupled to tert-butyloxycarbonyl-threonine (Boc-Thr) using dicyclohexylcarbodiimide and 1-hydroxybenzotriazole and the Boc-group was removed with trifluoroacetic acid. The resulting threonine N-methyl-benzylamide-2-boronate was coupled to the carboxylic acid group of LysB29 in des(B30) human insulin using achromobacter lyticus protease (Morihara and Ueno, Biotech. Bioeng. 1991, 37, 693). Subsequently, the ε-amino group of LysB29 was acylated selectively using N-hydroxysuccinimidyl lithocholate (U.S. Pat. No. 5,646,242) to give structure 3.

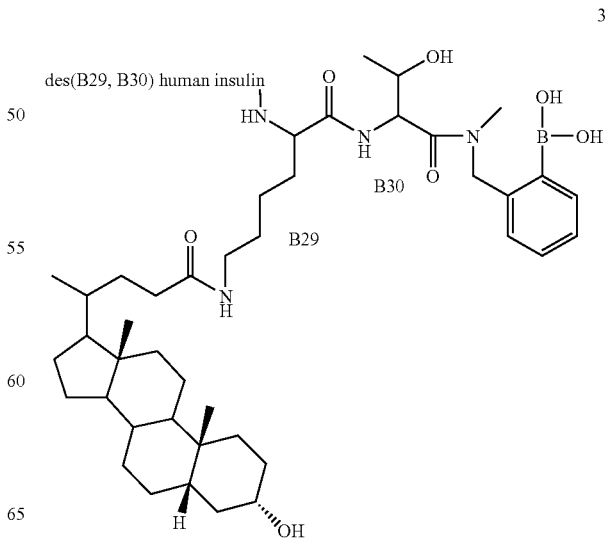

3

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 4

Lys$^{B29}$(N$^\epsilon$-lithocholoyl)-N'-methyl-N'-(benzyl-2-boronic acid)-2-amino-N-methyl-B30-ethylamide human insulin, 4

2,2-Dimethylpropane-1,3-diyl-2-(bromomethyl)phenylboronate (Bielecki, Eggert and Norrild, J. Chem. Soc. Perkin Trans 2, 1999, 449) was reacted with N',N-dimethylethylendiamine to give N'-methyl-N-methyl-N-benzyl-2-(2,2-dimethylpropane-1,3-diyl)boronate. This amine was coupled to tert-butyloxycarbonyl-threonine using dicyclohexylcarbodimide and 1-hydroxybenzotriazole and the Boc-group was removed with trifluoroacetic acid. The resulting threonine N-methyl-N'-methyl-N'-benzyl-(2-(2,2-dimethylpropane-1,3-diyl)boronate) 2-amino-ethylamide was coupled to the carboxylic acid group of LysB29 in des(B30) human insulin using achromobacter lyticus protease (Morihara and Ueno, Biotech. Bioeng. 1991, 37, 693). Subsequently, the ε-amino group of LysB29 was acylated selectively using N-hydroxysuccinimidyl lithocholate (U.S. Pat. No. 5,6461,242) to give structure 4.

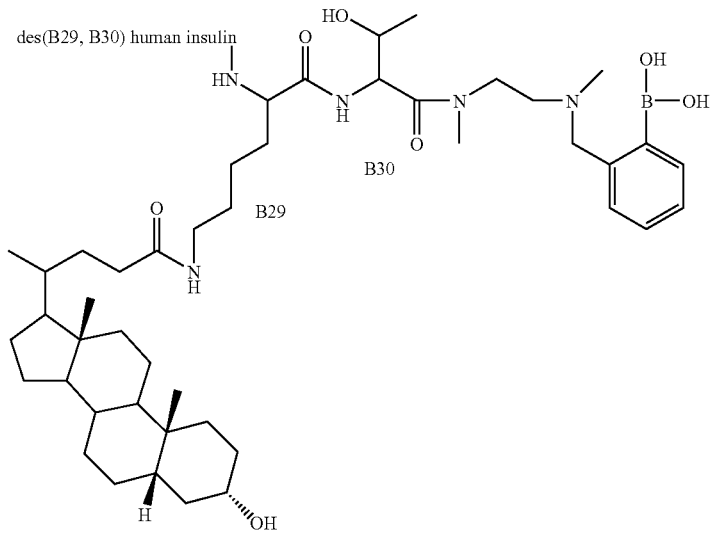

4

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 5

Lys$^{B29}$(N$^\epsilon$-lithocholoyl)-N'-(benzoyl-3-borno-5-nitro)-2-amino-N-phenyl-B30-ethylamide des(B30) human insulin, 5

3-Borono-5-nitro-benzoic acid (Combi-Blocks, San Diego, Calif., USA) was coupled to N-phenyl ethylenediamine using dicyclohexylcarbodimide and 1-hydroxybenzotriazole. The resulting N'-(3-borono-5-nitro-benzoyl) N-phenyl ethylenediamine was coupled to the carboxylic acid group of LysB29 in des(B30) human insulin using achromobacter lyticus protease (Morihara and Ueno, Biotech. Bioeng. 1991, 37, 693). Subsequently, the ε-amino group of LysB29 was acylated selectively using N-hydroxysuccinimidyl lithocholate (U.S. Pat. No. 5,646,242) to give structure 5.

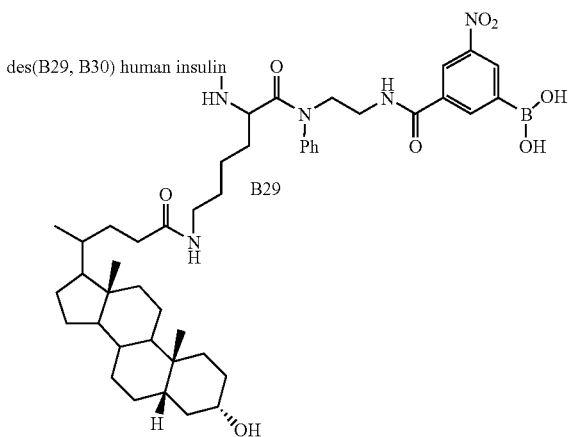

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 6

Lys$^{B29}$(N$^\epsilon$-lithocholoyl)-2-(pyridinium-3-boronic acid)-acetyl-2-amino-N-phenyl-B30-ethylamide des(B30) human insulin, 6

2,2-Dimethylpropane-1,3-diyl-3-borono-pyridine (Eggert, Frederiksen, Morin and Norrild, J. Org. Chem. 1999, 64, 3846) was reacted with bromoacetic acid. The resulting 2-(2,2-dimethylpropane-1,3-diyl-3-borono pyridinium) acetic acid was coupled to N-phenyl ethylenediamine using dicyclohexylcarbodimide and 1-hydroxybenzotriazole. The resulting amine was coupled to the carboxylic acid group of LysB29 in des(B30) human insulin using achromobacter lyticus protease (Morihara and Ueno, Biotech. Bioeng. 1991, 37, 693). Subsequently, the $\epsilon$-amino group of LysB29 was acylated selectively using N-hydroxysuccinimidyl lithocholate (U.S. Pat. No. 5,646,242) to give structure 6.

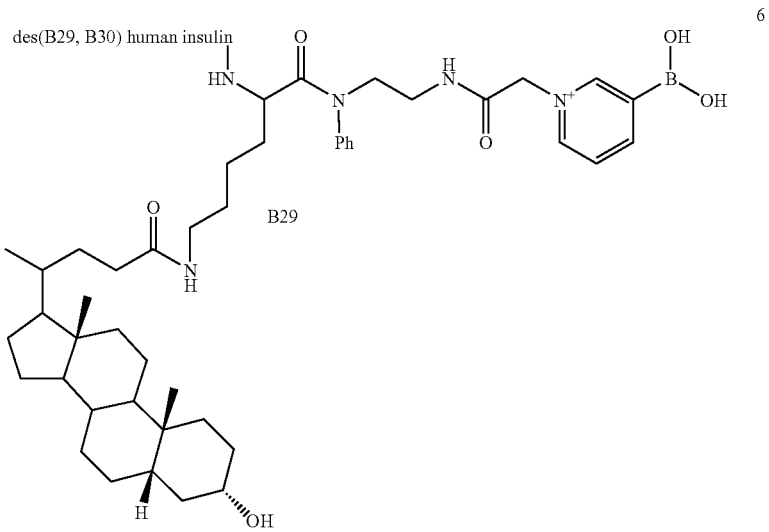

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 7

Lys$^{B29}$(N$^\epsilon$-tetradecanoyl)-B29-anilide-3-boronic acid des(B30) human insulin, 7

Aniline-3-boronic acid was coupled to the carboxylic acid group of LysB29 in des(B30) human insulin using achromobacter lyticus protease (Morihara and Ueno, Biotech. Bioeng. 1991, 37, 693). Subsequently, the $\epsilon$-amino group of LysB29 was acylated selectively using N-hydroxysuccinimidyl tetradecanoylate (U.S. Pat. No. 5,646,242) to give structure 7.

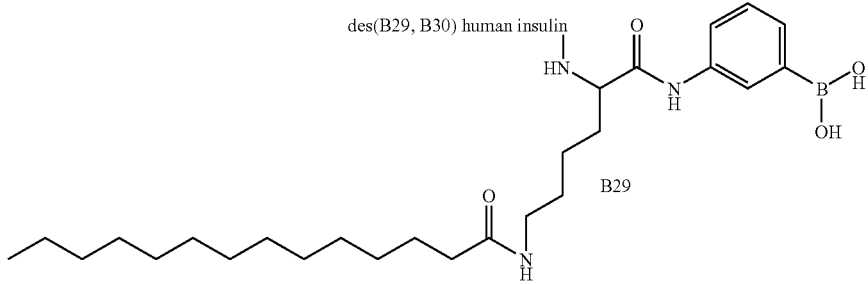

Using the above procedure, related compounds can be obtained by substituting N-hydroxysuccinimidyl tetradecanoylate with another N-hydroxysuccinimidyl ester of an acid having a lipophilic acid residue, for example lithocholic acid, hyocholic acid, hyodeoxycholic acid or chenodeoxycholic acid.

Example 8

Lys$^{B29}$(N$^\epsilon$-lithocholoyl)-Ams$^{B30}$ human insulin, 8

Ams(Boc)-OBu$^t$ (Spetzler and Hoeg-Jensen, J. Pept. Sci. 1999, 5, 582) was coupled to the carboxylic acid group of LysB29 in des(B30) human insulin using achromobacter lyticus protease (Morihara and Ueno, Biotech. Bioeng. 1991, 37, 693). Subsequently, the $\epsilon$-amino group of LysB29 was acylated selectively using N-hydroxy-succinimidyl lithocholate (U.S. Pat. No. 5,646,242) and the insulin was deprotected with trifluoroacetic acid to give structure 8.

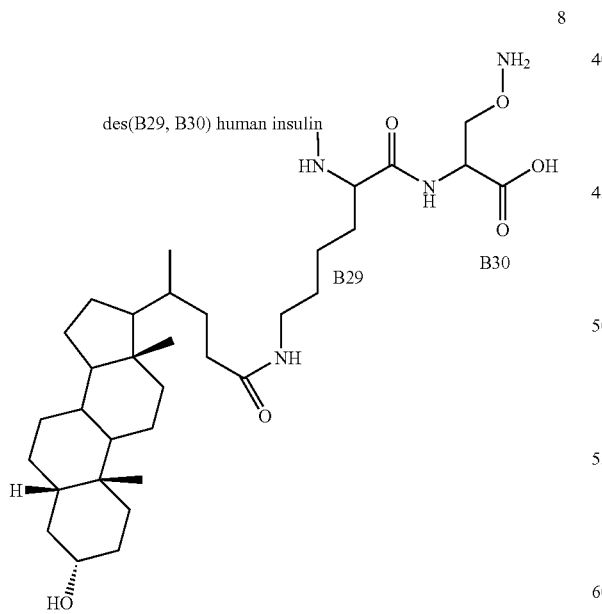

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 9

Phe$^{B26}$(3-(N,N-dimethyl-aminomethyl)-4-boronic acid),Lys$^{B29}$(N$^\epsilon$-lithocholoyl) des(B30) human insulin, 9

3-(N,N-Dimethyl-aminomethyl)-4-borono-phenylalanine (NBPhe) was made from 4-boronophenylalanine (RSP, Worchester, Mass., USA) and incorporated into the following peptide sequence using standard solid-phase peptide synthesis, Gly-Phe-Phe-NBPhe-Thr-Pro-Lys(lithocholoyl) SEQ ID NO: 18. This peptide was coupled to des-octapeptide human insulin using trypsin.

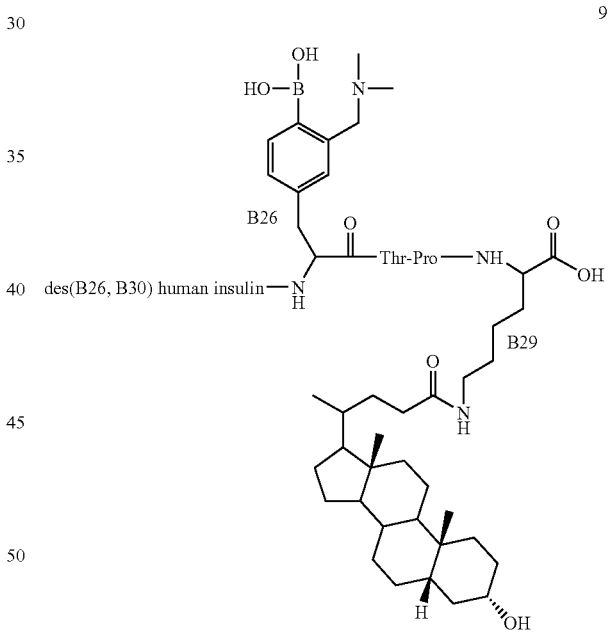

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 10

Lys$^{B29}$(N$^\epsilon$-cholanoyl-3-boronic acid) des(B30) human insulin, 10

3-Borono-cholanoyl was made from lithocholic acid by elimination (Templeton et al. Steroids 2000, 65, 219) and hydroboration (Kirk et al. J. Chem. Soc. Perkin Trans 1 1976, 1836). The lithocholate was converted to its N-hydroxysuccinimidyl ester which was used to acylate the ε-amino group of LysB29 in des(B30) human insulin selectively (U.S. Pat. No. 5,646,242).

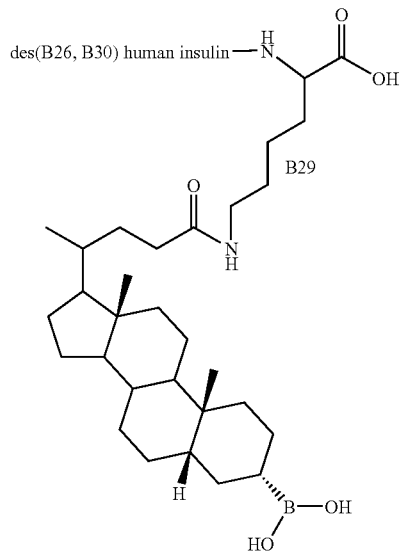

Using the above procedure, related compounds can be obtained by substituting N-hydroxysuccinimidyl cholanoylate with another N-hydroxysuccinimidyl ester of an acid having a lipophilic acid residue, for example the 6,7-dihydroxycholanoylate, the 6-hydroxycholanoylate or the 7-hydroxycholanoylate.

Example 11

Lys$^{B29}$(N$^\epsilon$-(lithocholoyl-(4-methyl-aminomethyl-3-boronic acid-benzoyl))) des(B30) human insulin, 11

4-Methyl-aminomethyl-3-borono-benzoic acid (Combi-Blocks, San Diego, Calif., USA) was N-acylated using N-hydroxysuccinimidyl lithocholate as acylating agent. The resulting lithocholyl benzoic acid was converted to its N-hydroxysuccinimidyl ester and used to selectively acylate the ε-amino group of LysB29 in des(B30) human insulin (U.S. Pat. No. 5,646,242) to give structure 11.

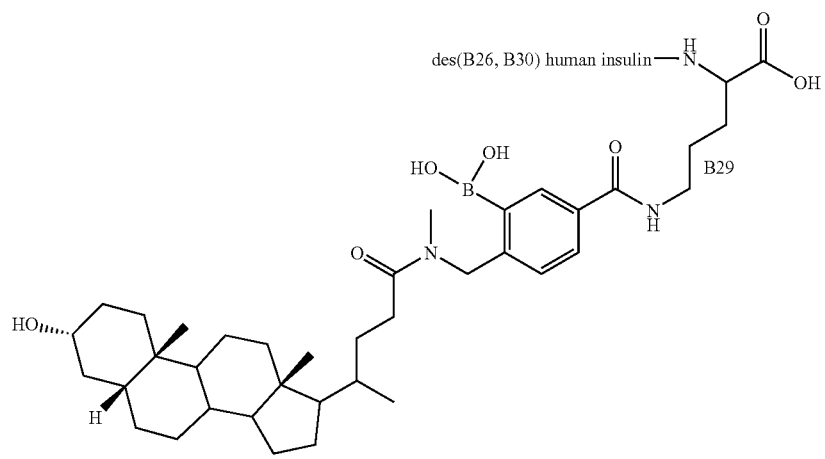

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 12

Lys$^{B29}$(N$^\epsilon$-Lithocholoyl)-4-N-(benzyl-2-boronic acid)-4-amine-B29-anilide des(B30) human insulin, 12

2,2-Dimethylpropane-1,3-diyl-2-(bromomethyl)phenyl-boronate (Bielecki, Eggert and Norrild, J. Chem. Soc. Perkin Trans 2, 1999, 449) was reacted with 1,4-phenylene-diamine to give 1,4-phenylenediamine-N-benzylamine-2-(2,2-dimethylpropane-1,3-diyl)boronate. This amine was coupled to the carboxylic acid group of LysB29 in des(B30) human insulin using achromobacter lyticus protease (Morihara and Ueno, Biotech. Bioeng. 1991, 37, 693). Subsequently, the ε-amino group of LysB29 was acylated selectively using N-hydroxysuccinimidyl lithocholate (U.S. Pat. No. 5,646,242) to give structure 12.

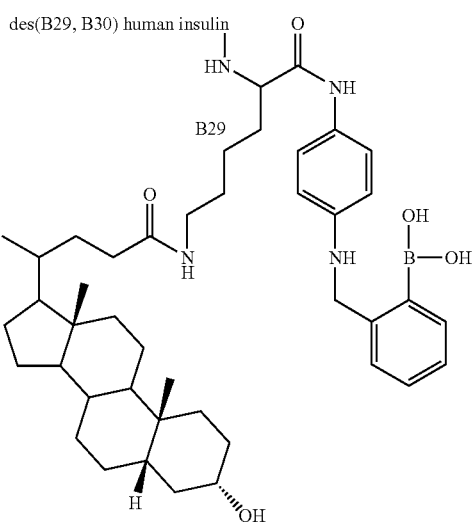

12

Using the above procedure, related compounds can be obtained by substituting N-hydroxysuccinimidyl lithocholate with another N-hydroxysuccinimidyl ester of an acid having a lipophilic acid residue, for example hyocholic acid, hyodeoxycholic acid or chenodeoxycholic acid.

Example 13

Lys$^{B29}$(N$^\epsilon$-(ω-carboxamidophenyl-3-boronic acid nonadecanoyl)) des(B30) human insulin 13

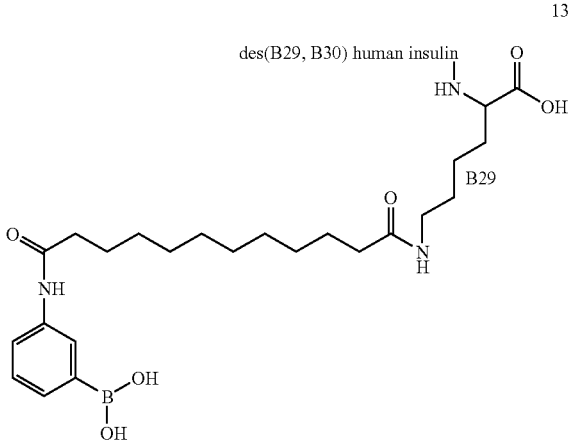

13

The mono hydroxysuccinimidyl ester of α,ω-dodecanedicarboxylic was reacted with 3-borono-aniline. The resulting ω-carboxamidophenyl-3-boronic acid nonadecanoyl was converted to its hydroxysuccinimidyl ester. This ester was used to acylate the ε-amino group of des(B30) human insulin selectively to give the desired derivative (U.S. Pat. No. 5,646,242).

Example 14

Synthesis of N-succinimidyl tert-butyloxycarbonylaminoxy acetate, Boc-AOA-OSu tert-Butyloxycarbonylaminoxy acetic acid was dissolved in ice-cooled ethyl acetate or acetonitrile and treated with N,N'-dicyclohexylcarbodiimide (1.0 equivalent) and N-hydroxysuccinimide (1.0 equivalent). The reaction mixture was stirred at room temperature overnight. The N,N'-dicyclohexylurea formed was removed by filtration and the filtrate was evaporated to dryness in vacuo. The crude Boc-AOA-OSu was either used directly in the next step or purified by recrystallisation from chloroform. Adopted from Kurth et al. J. Med. Chem. 1993, 36, 1255.

Example 15

Synthesis of Lys$^{B29}$(AOA) des(B30) human insulin 15

Des(B30) human insulin (1 g) was dissolved in 50 ml 0.05 M boric acid by adjusting the pH to 10.2 with 1N NaOH and placed in a thermostat at 15° C. To the solution was added 61 mg of Boc-AOA-OSu dissolved in 50 ml acetonitrile. The reaction was stopped after 1 h by addition of 19 ml 0.2N ethanolamine, pH 9.0. The product was precipitated by addition of water to a total volume of 250 ml, adjusting the pH to 5.5 with HCl and cooling the solution to −20° C. The precipitate was isolated by centrifugation at −10° C. and dried in vacuo. Mass spectrometry revealed the parent insulin compound, the monoacylated insulin, and diacylated insulin. The dried product was treated for 1 h at room temperature with 10 ml trifluoroacetic acid plus 0.3 ml triisopropylsilane. The reaction mixture was added dropwise to 100 ml of cold diethyl ether; and the precipitate formed was isolated and dried in vacuo. Finally, the compound 15 was purified by RP-HPLC at pH 4.0 using a gradient from 20 to 60% ethanol. Mw found by MALDI-MS: 5778 (theoretical value: 5780).

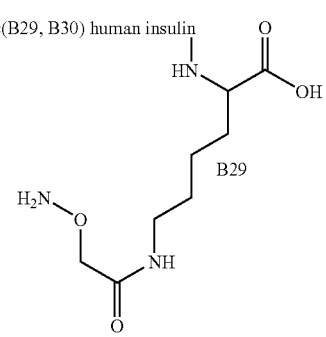

15

Example 16

Crystalline protamine preparation of Lys$^{B29}$(AOA) des(B30) human insulin 1. Stock solution of Lys$^{B29}$ (AOA) des(B30) human insulin. 35.0 mg Lys$^{B29}$(AOA) des(B30) human insulin was dissolved in water by addition of 32 µl 1N HCl, 375 µl m-cresol solution (20 mg/ml), 65 µl phenol solution (50 mg/ml), 80 mg glycerol, and 32.7 µl ZnCl$_2$ solution (10 mg/ml), finally adjusting the volume to 5 ml. The pH is about 3.
2. 2.25 ml of this stock solution was mixed with 197 µl of a 10 mg/ml solution in water of protamine sulfate.
3. To the resulting mixture was added 2.25 ml of a sodium phosphate buffer (pH 8.0) comprising 375 µl m-cresol solution (20 mg/ml), 65 µl phenol solution (50 mg/ml), 80 mg glycerol, 1.85 ml 70 mM Na$_2$PO$_4$, and the volume was adjusted to 5 ml with water. The pH of the second mixture was about 5–6, and an amorphous precipitate of Lys$^{B29}$ (AOA) des(B30) insulin and protamine was formed. The pH was adjusted to 7.3 with 1 N NaOH. Crystals of Lys$^{B29}$ (AOA) des(B30) insulin-protamine appeared on standing at room temperature.

Example 17

Lys$^{B29}$(N$^\epsilon$-(γ-glutamyl-N$^\alpha$-lithocholoyl),Lys$^{B30}$(N$^\epsilon$-3-nitro-5-boronobenzoyl) human insulin, 17

3-Nitro-5-boronobenzoic acid (Combi Blocks, San Diego, USA) was reacted with pinacole in THF and MgSO$_4$. The resulting 3-nitro-5-pinacolboronobenzoic acid was reacted with N-hydroxysuccinimide and DCC in THF. The succinimide ester was reacted with N$^\alpha$-tert-butyloxycarbonyl-lysine (Bachem) in DMF and triethylamine. The resulting N$^\alpha$-tert-butyloxycarbonyl,N$^\epsilon$-3-nitro-5-pinacolborono-lysine was treated with methanol and trimethylsilyl chloride, 10:1, to give N$^\epsilon$-3-nitro-5-pinacolboronobenzoyl methyl lysinate, hydrochloride:

$^1$H-NMR (CDCl$_3$) δ: 8.84 (dd, 1H, ArH), 8.71 (bd, 3H, NH$_3$$^+$), 8.61 (dd, 1H, ArH), 8.54 (dd, 1H, ArH), 7.98 (s, 1H, NH), 4.17 (m, 1H, αCH), 3.75 (s, 3H, CH$_3$), 3.48 (m, 2H, CH$_2$N), 2.09 (m, 2H, CH$_2$), 1.72 (m, 3H, βCH+CH$_2$), 1.57 (m, 1H, βCH'), 1.31 (s, 12H, pinacolyl).

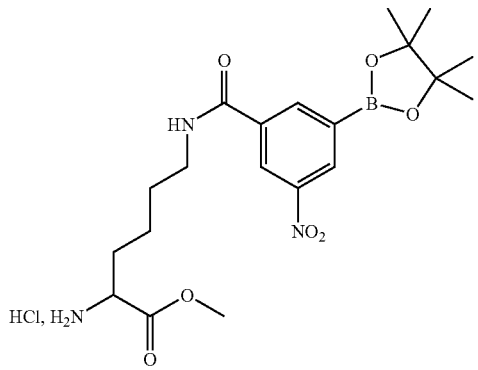

This amino acid derivative was coupled to the carboxylic acid group of LysB29 in des(B30) human insulin using achromobacter lyticus protease (Morihara and Ueno, Biotech. Bioeng. 1991, 37, 693) in NMP-water to give 17a (yield: 70%. Mw found by ESMS: 6041 (theoretical value: 6041)). Subsequently, the ε-amino group of LysB29 was acylated selectively using γ-N-hydroxysuccinimidyl α-methyl glutamyl-N$^\alpha$-lithocholate in acetonitrile-water, pH 10, (U.S. Pat. No. 5,646,242) and the methyl ester was saponified to give structure 17 (yield: 53%. Mw found by ESMS: 6513 (theoretical value: 6515)).

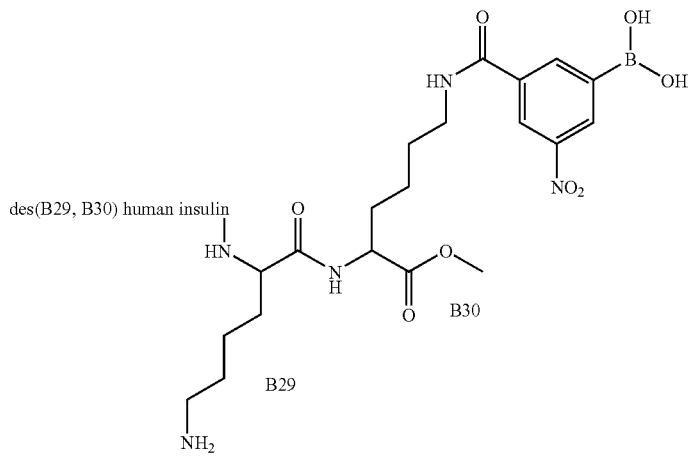

17a

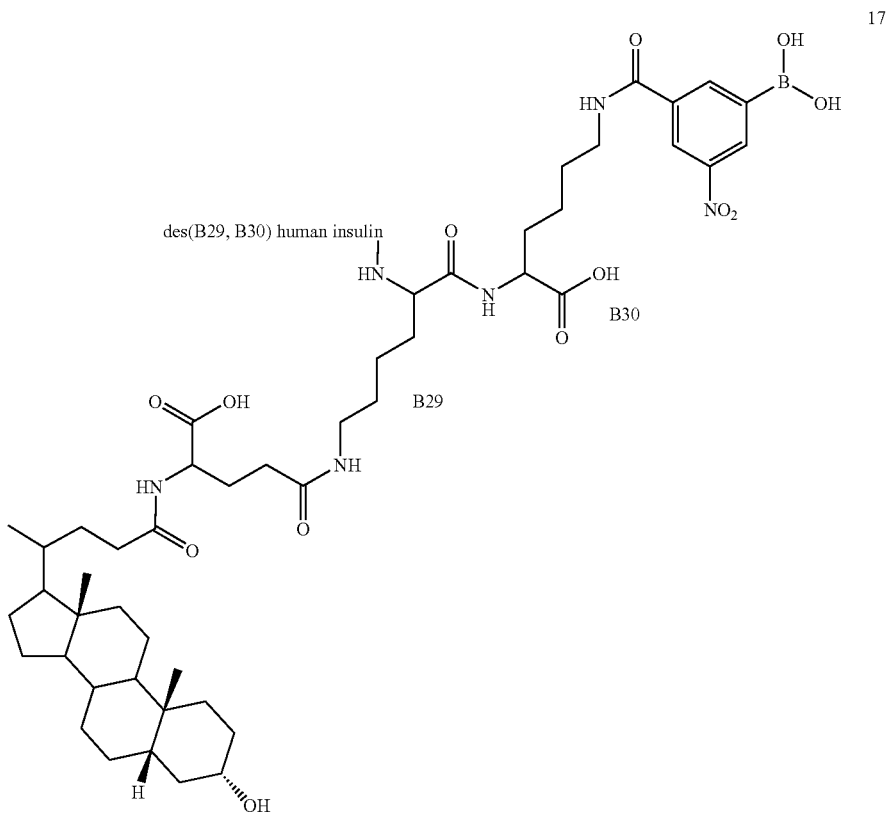

Example 18

Lys$^{B29}$(N$^\epsilon$-(γ-glutamyl-N$^\alpha$-lithocholoyl),Orn$^{B30}$(N$^\epsilon$-3-nitro-5-boronobenzoyl) human insulin, 18

The Orn$^{B30}$ analogue of 17 was prepared by a method corresponding to the method used for the preparation of 17.

N$^\epsilon$-3-nitro-5-pinacolboronobenzoyl, methyl ornitate, hydrochloride:

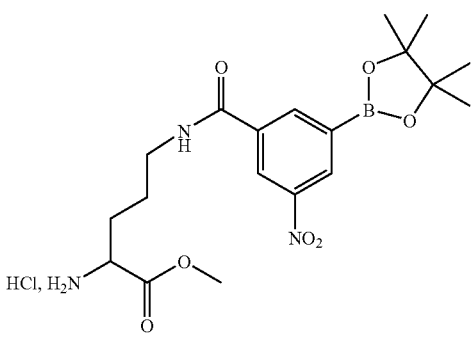

$^1$H-NMR (CDCl$_3$) δ: 8.82 (dd, 1H, ArH), 8.71 (bd, 3H, NH$_3{}^+$), 8.59 (dd, 1H, ArH), 8.54 (dd, 1H, ArH), 8.07 (s, 1H, NH), 4.26 (m, 1H, αCH), 3.72 (s, 3H, CH$_3$), 3.51 (m, 2H), CH$_2$N), 2.16 (m, 2H, CH$_2$), 1.89 (m, 2H, CH$_2$), 1.32 (s, 12H, pinacolyl).

18a, yield: 59%. Mw found by ESMS: 6028 (theoretical value: 6027).

18, yield: 62%. Mw found by ESMS: 6501 (theoretical value: 6501).

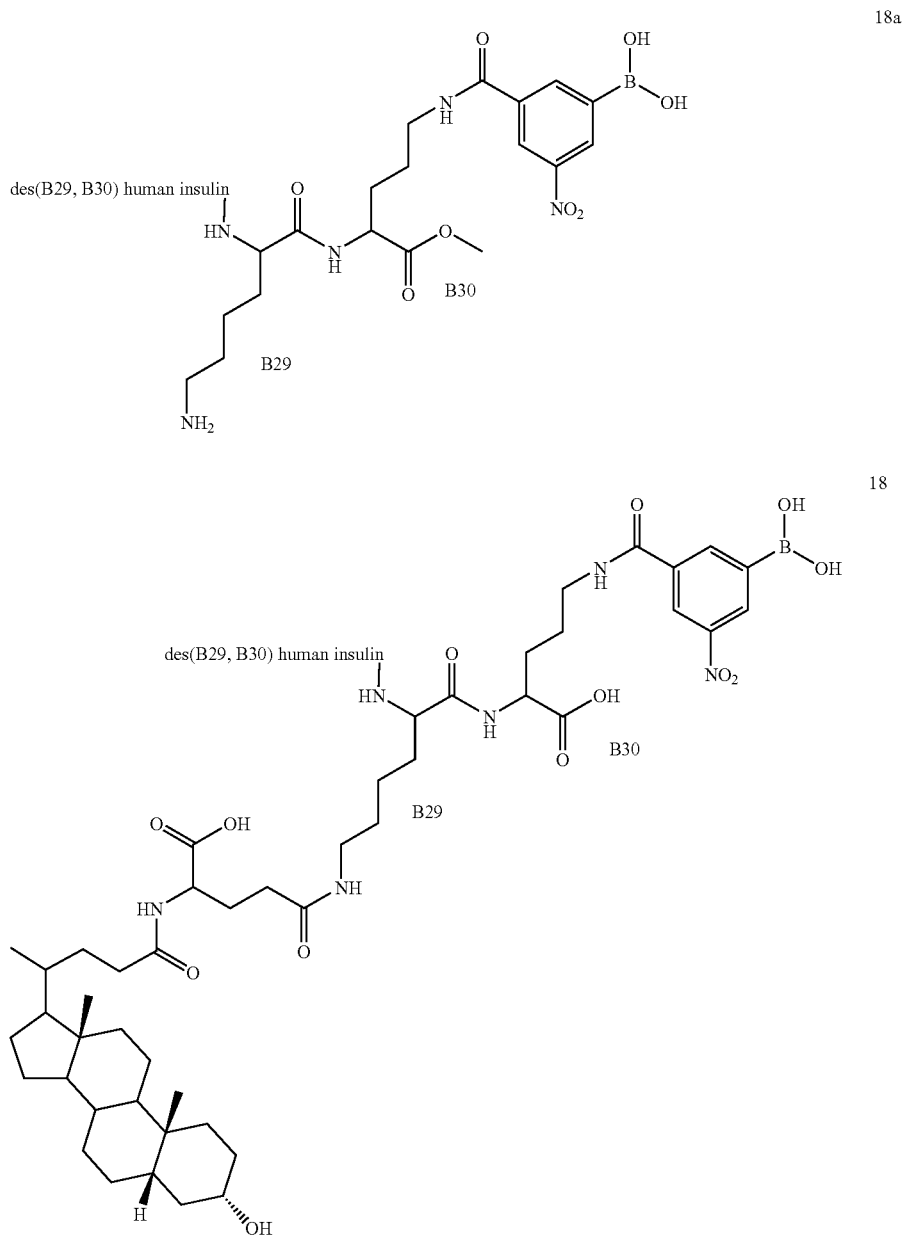

18a

18

Example 19

Lys$^{B29}$(N$^\epsilon$-(γ-glutamyl-N$^\alpha$-lithocholoyl),Dap$^{B30}$(N$^\epsilon$-3-nitro-5-boronobenzoyl) human insulin, 19

The Dap$^{B30}$ analogue of 17 was prepared by a method corresponding to the method used for the preparation of 17.

N$^\epsilon$-3-nitro-5-pinacolboronobenzoyl, methyl diaminopropionate, hydrochloride:

$^1$H-NMR (CDCl$_3$) δ: 8.90 (dd, 1H, ArH), 8.84 (bd, 3H, NH$_3^+$), 8.68 (dd, 1H, ArH), 8.55 (dd, 1H, ArH), 6.25 (s, 1H, NH), 4.55 (m, 1H, αCH), 4.26 (m, 1H, βCH), 4.07 (m, 1H, βCH'), 1.32 (s, 12H, pinacolyl).

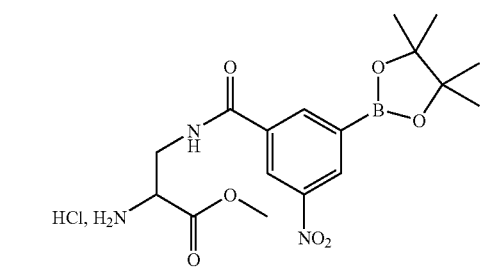

19a, yield: 60%. Mw found by ESMS: 6000 (theoretical value: 5999).

19, yield: 56%. Mw found by ESMS: 6473 (theoretical value: 6473).

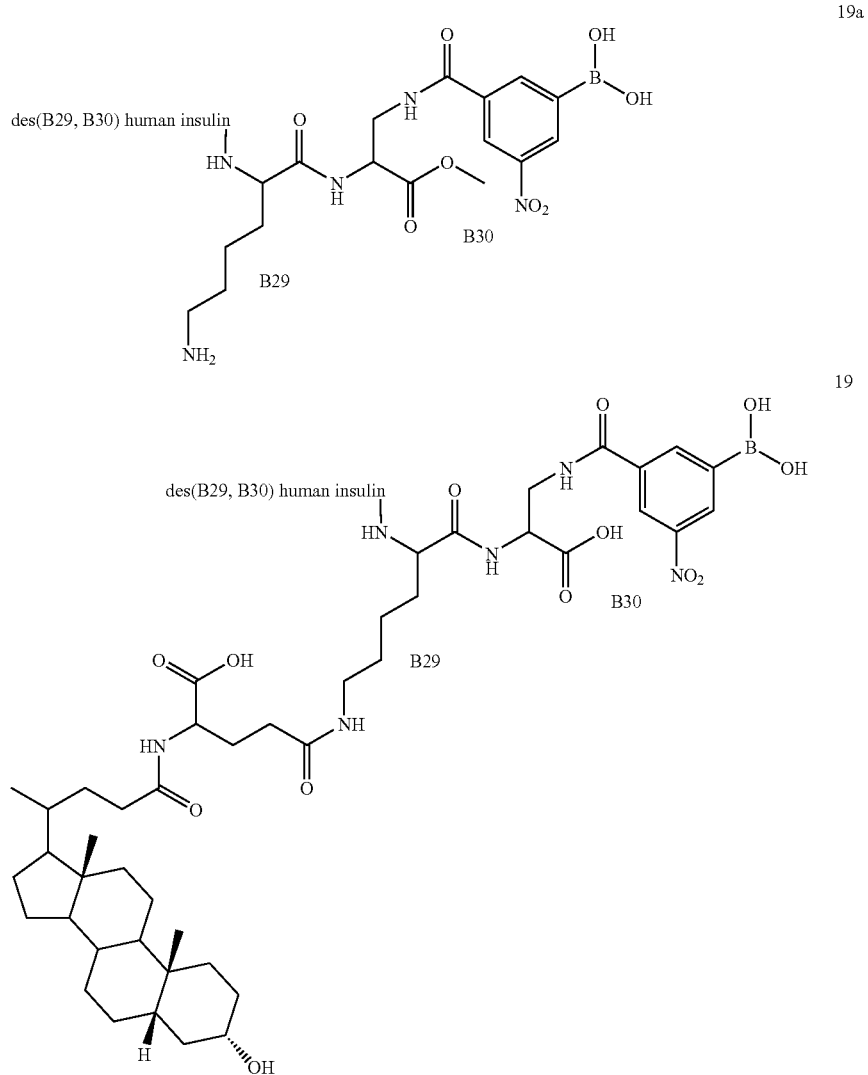

Example 20

Lys$^{B29}$(N$^\epsilon$-(γ-glutamyl-N$^\alpha$-lithocholoyl),Lys$^{B30}$ (N$^\epsilon$-4-boronobenzoyl) human insulin, 20

4-Pinacolboronobenzoic acid (Aldrich Fine Chemicals) was reacted with N-hydroxysuccinimide and DCC in THF. The succinimide ester was reacted with N$^\alpha$-tert-butyloxycarbonyl-lysine (Bachem) in DMF and triethylamine. The resulting N$^\alpha$-tert-butyloxycarbonyl, N$^\epsilon$-4-pinacolboronolysine was treated with methanol and trimethylsilyl chloride, 10:1, to give N$^\epsilon$-4-pinacolboronobenzoyl, methyl lysinate, hydrochloride:

$^1$H-NMR (CDCl$_3$) δ: 9.04 (bs, 1H, NH), 8.71 (bs, 3H, NH$_3^+$), 7.90 (d, 2H, ArH), 7.80 (d, 2H, ArH), 4.13 (m, 1H, αCH), 3.74 (s, 3H, CH$_3$), 3.47 (m, 2H, CH$_2$N), 2.69 (m, 2H, CH$_2$), 2.07 (m, 2H, CH$_2$), 1.67 (m, 3H, βCH+CH$_2$), 1.54 (m, 1H, βCH), 1.32 (s, 12H, pinacolyl).

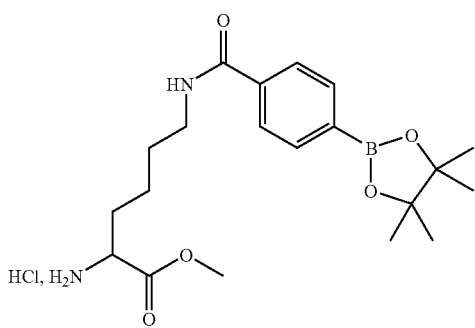

This amino acid derivative was coupled to the carboxylic acid group of LysB30 in des(B30) human insulin using achromobacter lyticus protease (Morihara and Ueno, Biotech. Bioeng. 1991, 37, 693) to give 20a (yield: 53%. Mw found by ESMS: 6000). Subsequently, the ε-amino group of LysB29 was acylated selectively using γ-N-hydroxysuccinimidyl α-methyl glutamyl-N^α-lithocholate (U.S. Pat. No. 5,646,242) and the methyl ester groups were saponified to give structure 20 (yield: 61%. Mw found by ESMS: 6470).
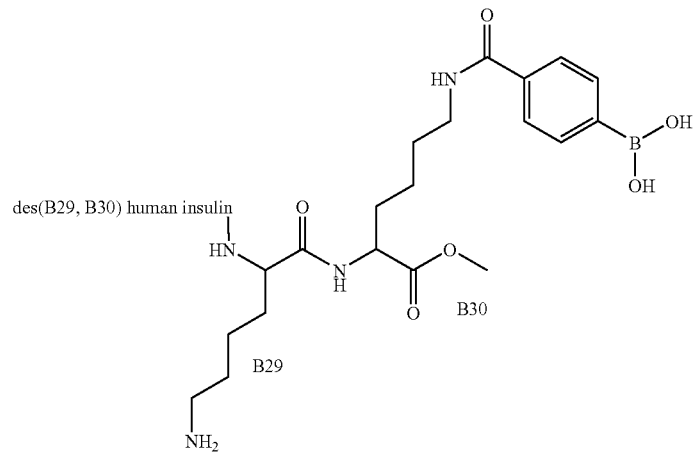
20a
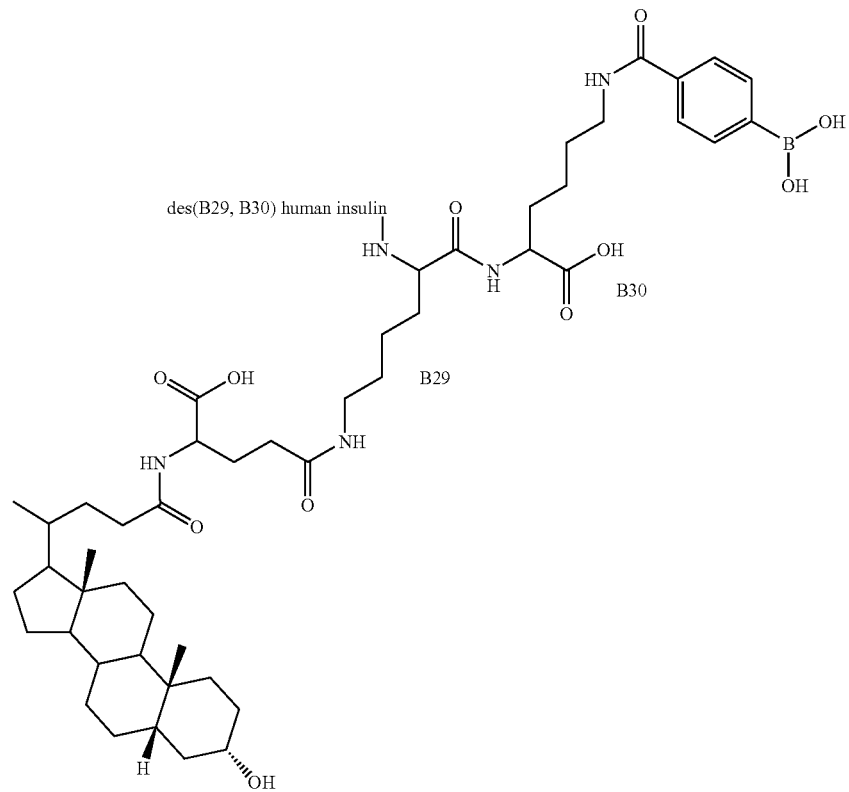
20

Example 21

Lys$^{B29}$(N$^\epsilon$-(γ-glutamyl-N$^\alpha$-lithocholoyl),Orn$^{B30}$(N$^\epsilon$-4-boronobenzoyl) human insulin, 21

The Orn$^{B30}$ analogue of 20 was prepared by a method corresponding to the method used for the preparation of 20.

N$^\epsilon$-4-pinacolboronobenzoyl, methyl ornitanate, hydrochloride:

$^1$H-NMR (CDCl$_3$) δ: 8.90 (bs, 1H, NH), 8.69 (bs, 3H, NH$_3^+$), 7.88 (d, 2H, ArH), 7.80 (d, 2H, ArH), 4.21 (m, 1H, αCH), 3.69 (s, 3H, CH$_3$), 3.50 (m, 2H, CH$_2$N), 2.66 (m, 2H, CH$_2$), 2.12 (m, 1H, βCH), 1.88 (m, 1H, βCH), 1.29 (s, 12H, pinacolyl).

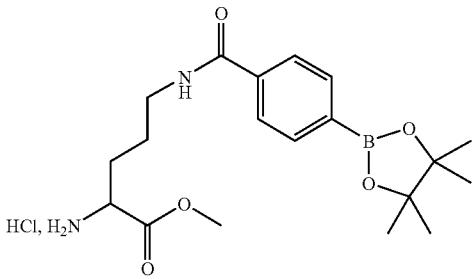

21a, yield: 56%. Mw found by ESMS: 5983 (theoretical value: 5985).

21, yield: 62%. Mw found by ESMS: 6456 (theoretical value: 6456).

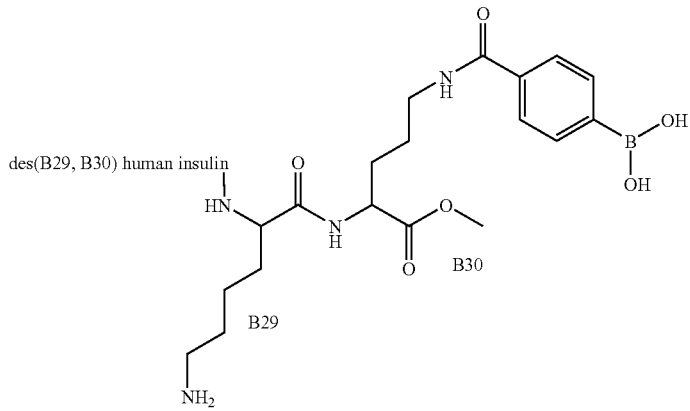

21a

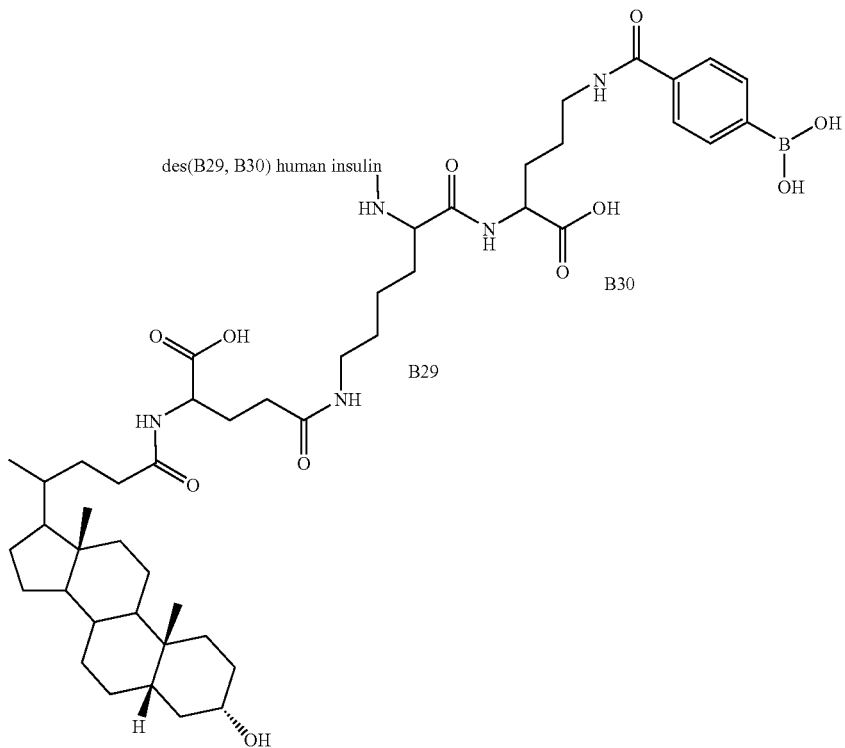

21

Lys$^{B29}$(N$^\epsilon$-(γ-glutamyl-N$^\alpha$-lithocholoyl),Dab$^{B30}$(N$^\epsilon$-4-boronobenzoyl) human insulin, 22

The Dab$^{B30}$ analogue of 20 was prepared by a method corresponding to the method used for the preparation of 20.

N$^\epsilon$-4-pinacolboronobenzoyl, methyl diaminobutyrate, hydrochloride:

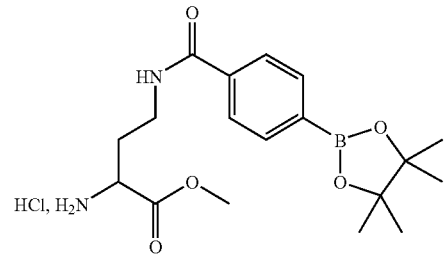

$^1$H-NMR (CDCl$_3$) δ: 8.96 (bs, 1H, NH), 8.88 (bs, 3H, NH$_3$$^+$), 7.87 (d, 2H, ArH), 7.77 (d, 2H, ArH), 4.29 (m, 1H, αCH), 3.75 (m, 1H, CHN), 3.64 (m, 1H, CH'N), 3.56 (s, 3H, CH$_3$), 2.47 (m, 2H, βCH), 1.31 (s, 12H, pinacolyl).

22a, yield: 71%. Mw found by ESMS: 5969 (theoretical value: 5973).

22, yield: 59%. Mw found by ESMS: 6442 (theoretical value: 6442).

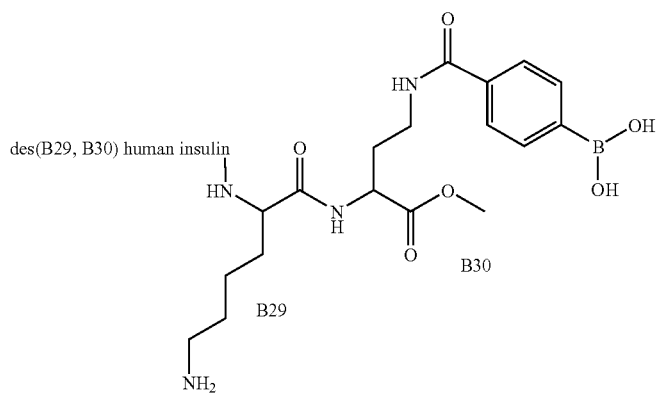

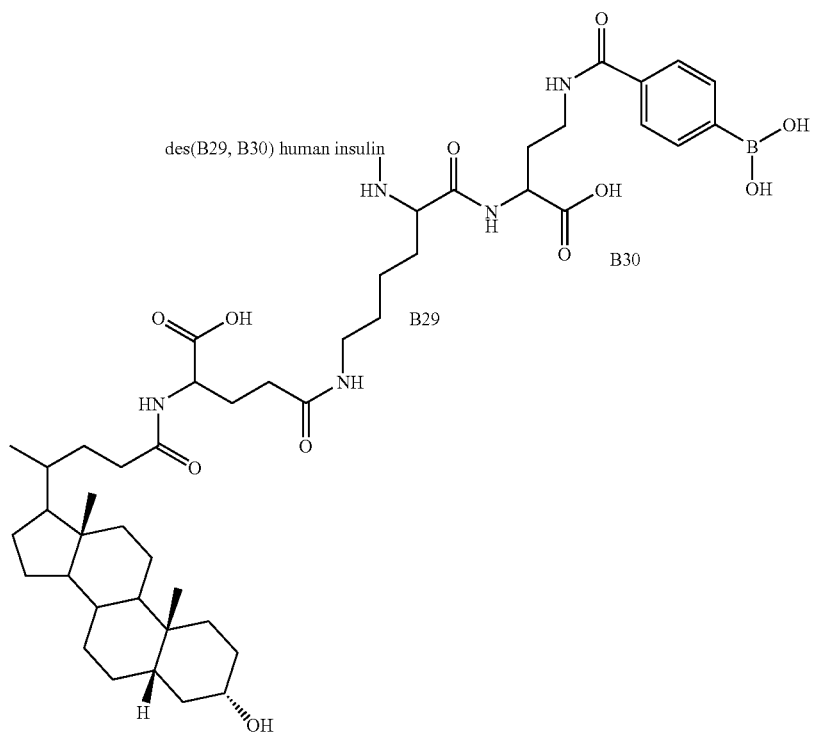

Example 23

Lys$^{B29}$(N$^\epsilon$-(γ-glutamyl-N$^\alpha$-lithocholoyl),Orn$^{B30}$(N$^\epsilon$-4-boronobenzenesulfonyl) human insulin, 23

4-Bromobenzene sulfonyl chloride (Aldrich Fine Chemicals) was reacted with N$^\alpha$-tert-butyloxycarbonyl methyl ornitate acetate (Chemlmpex, Illinois, USA) in DMF and TEA. The resulting bromide was reacted with bis(pinacol) diborone and 1,1'-bis(diphenylphosphino)ferrocenedichloropalladium(II) in dioxane with potassium acetate (Ishiyama et al. J. Org. Chem. 1995, 60, 7508). The resulting N$^\alpha$-tert-butyloxycarbonyl, N$^\epsilon$-(4-pinacolborono-benzenesulfonyl)-lysine was treated with methanol and trimethylsilyl chloride, 10:1, to give N$^\epsilon$-(4-pinacolborono-benzenesulfonyl), methyl ornitate, hydrochloride:

$^1$H-NMR (DMSO-d$_6$) δ: 8.57 (bs, 3H, NH$_3$$^+$), 7.87 (dd, 4H, ArH), 6.66 (t, 1H, NHSO$_2$), 4.31 (m, 1H, αH), 3.77 (s, 3H, CH$_3$), 2.93 (m, 2H, CH$_2$N), 2.15 (m, 2H, CH$_2$), 1.85 (m, 1H, βCH), 1.75 (m, 1H, βCH'), 1.34 (s, 12H, pinacolyl).

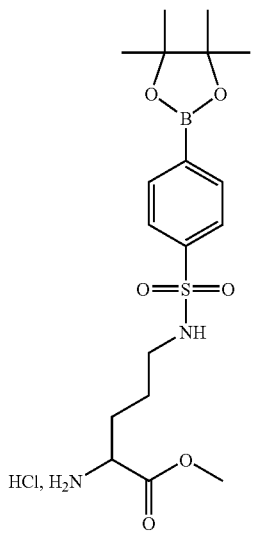

This amino acid derivative was coupled to the carboxylic acid group of LysB29 in des(B30) human insulin using achromobacter lyticus protease (Morihara and Ueno, Biotech. Bioeng. 1991, 37, 693) and the methyl ester was saponified to give 23a (yield: 30%. Mw found by ESMS: 6006 (theoretical value: 6005)). Subsequently, the ε-amino group of LysB29 was acylated selectively using γ-N-hydroxysuccinimidyl α-methyl glutamyl-N$^\alpha$-lithocholate (U.S. Pat. No. 5,646,242) and the Glu methyl ester was saponified to give structure 23 (yield: 51%. Mw found by ESMS: 6493 (theoretical value: 6492)).

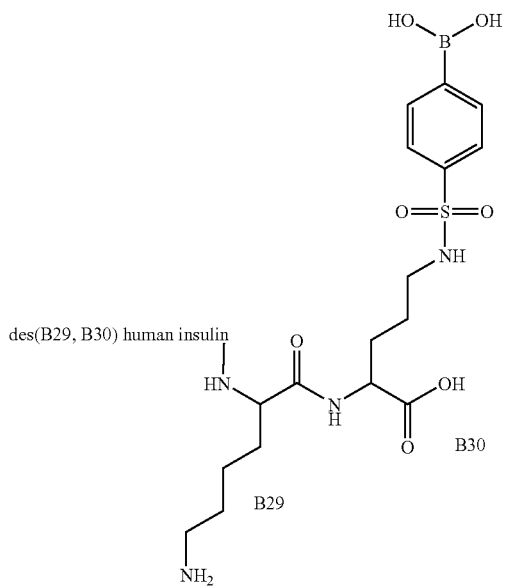

23a

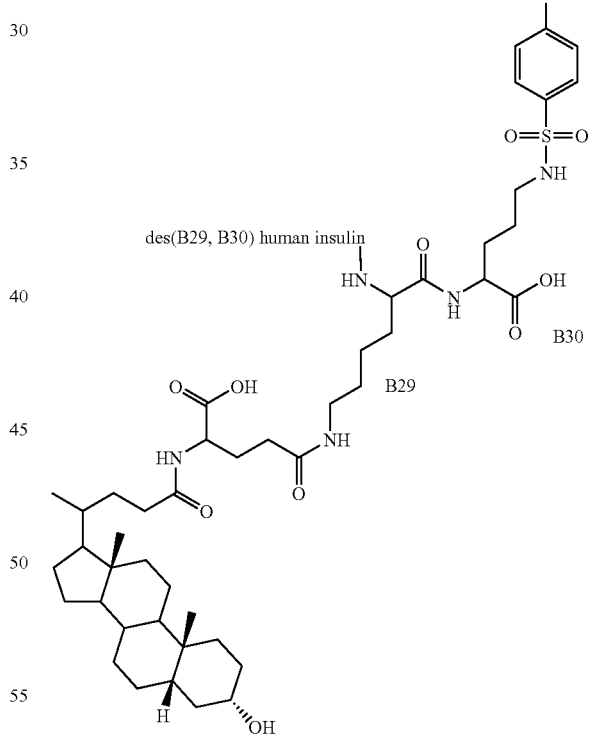

23

Example 24

Lys$^{B29}$(N$^\epsilon$-(γ-glutamyl-N$^\epsilon$-lithocholoyl),Lys$^{B30}$(N$^\epsilon$-4-boronobenzenesulfony) human insulin, 24

The Lys$^{B30}$ analogue of 23 was prepared by a method corresponding to the method used for the preparation of 23.
N$^\epsilon$-(4-pinacolborono-benzenesulfonyl), methyl lysinate, hydrochloride:

¹H-NMR (CDCl₃) δ: 8.59 (bs, 2H, NH), 7.89 (m, 4H, ArH), 4.28 (m, 1H, αH), 3.81 (s, 3H, CH₃), 2.93 (m, 2H, CH₂N), 2.09 (m, 2H, CH₂), 1.76 (m, 1H, βCH), 1.58 (m, 3H, CH₂+βCH'), 1.34 (s, 12H, pinacolyl).

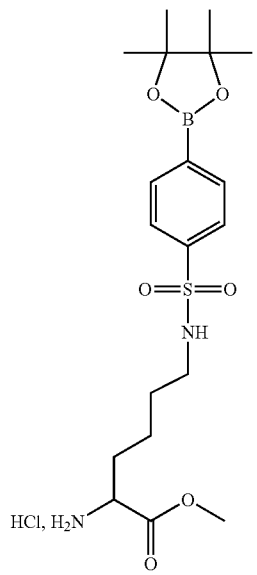

24a, yield: 53%. Mw found by ESMS: 6022 (theoretical value: 6020).

24, yield: 60%. Mw found by ESMS: 6507 (theoretical value: 6506).

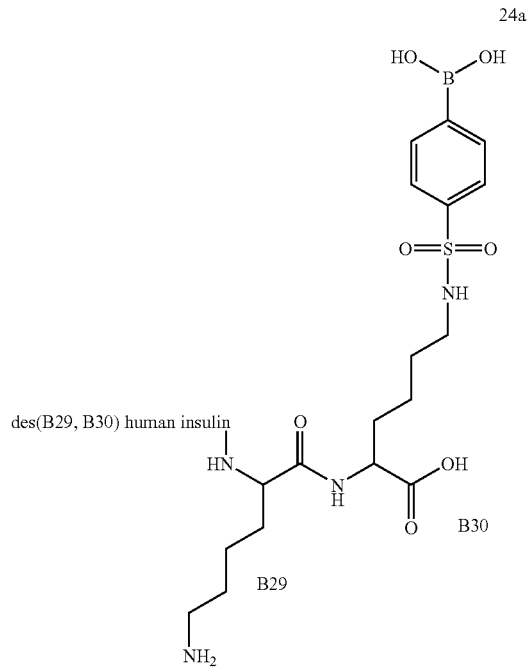

24a

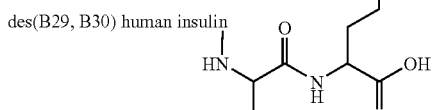
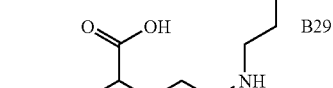
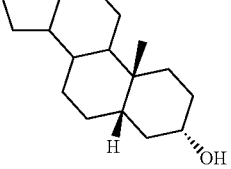

24

Example 25

Lys$^{B29}$(N$^\epsilon$-(γ-glutamyl-N$^\alpha$-lithocholoyl),Lys$^{B30}$(N$^\epsilon$-2,5-difluoro-4-boronobenzenesulfonyl) human insulin, 25

The Lys$^{B30}$(N$^\epsilon$-4-borno-2,5-difluoro-benzenesulfonyl) analogue of 23 was prepared by a method corresponding to the method used for the preparation used for 23.

N$^\epsilon$-(2,5-difluoro-4-pinacolborono-benzenesulfonyl), methyl lysinate, hydrochloride:

¹H-NMR (CDCl₃) δ: 8.42 (m, 3H, NH₃⁺), 7.49 (m, 2H, ArH), 6.40 (t, 1H, NHSO₂), 4.21 (m, 1H, αH), 3.82 (s, 3 H, CH₃), 3.05 (m, 2H, CH₂N), 2.05 (m, 2H, CH₂), 1.65 (m, 4H, 2×CH₂), 1.34 (s, 12H, pinacolyl).

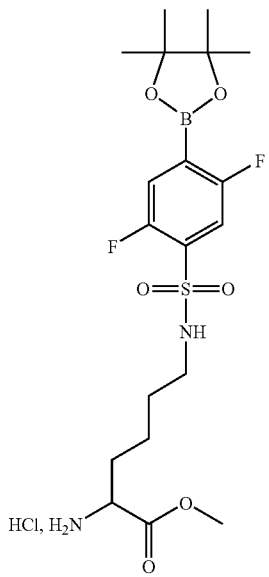

25a, yield: 71%. Mw found by ESMS: 6055 (theoretical value: 6054).

25, yield: 59%. Mw found by ESMS: 6542 (theoretical value: 6542).

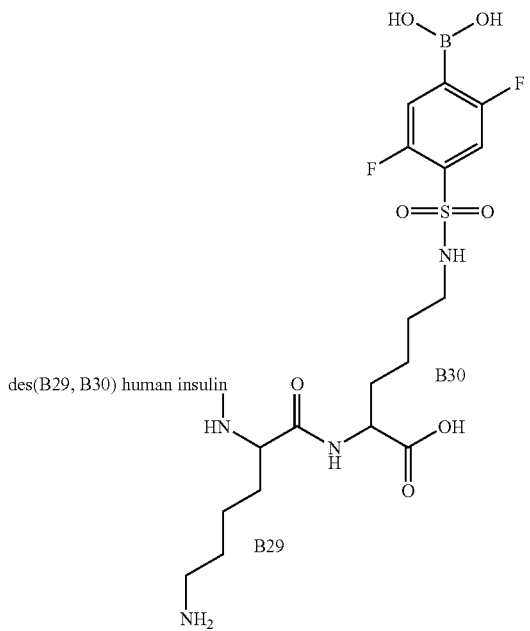

25a

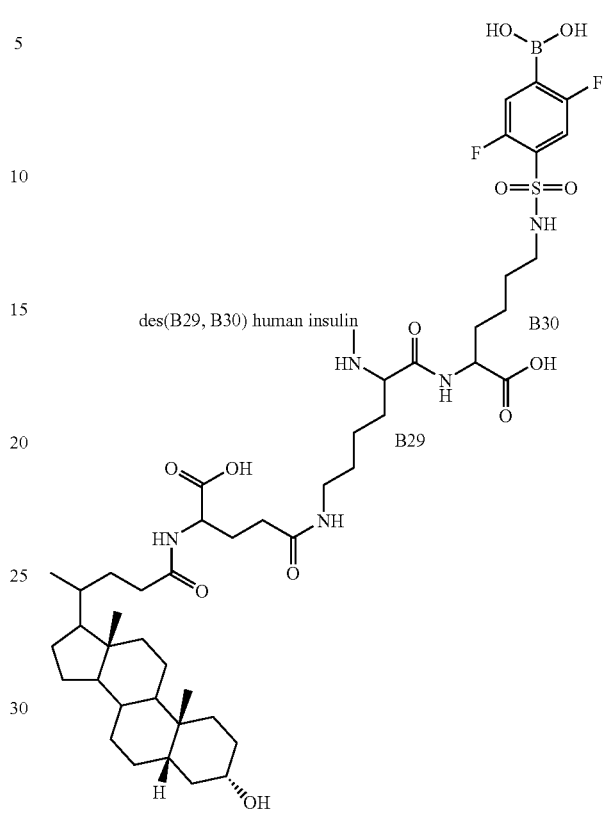

25

Example 26

Lys$^{B29}$(N$^\epsilon$-(γ-glutamyl-N$^\alpha$-lithocholoyl),Lys$^{B30}$(N'-(3-nitro-5-borono-benzoyl)-1,4-phenylendiamine) human insulin amide, 26

N-(tert-Butyloxycarbonyl)-phenylenediamine (Aldrich) was reacted with N-succinimidyl-3-nitro-5-pinacolboronobenzoate (see example 16) in THF. The Boc-group was removed using TFA to give N'-(3-nitro-5-borono-benzoyl)-1,4-phenylendiamine, triflouroacetate:

$^1$H-NMR (DMSO-d$_6$) δ: 10.78 (s, 1H, NH), 8.89 (s, 1H, ArH), 8.63 (s, 1H, ArH), 8.54 (s, 1H, ArH), 7.84 (d, 2H, ArH), 7.28 (d, 2H, ArH), 1.34 (s, 12H, pinacolyl).

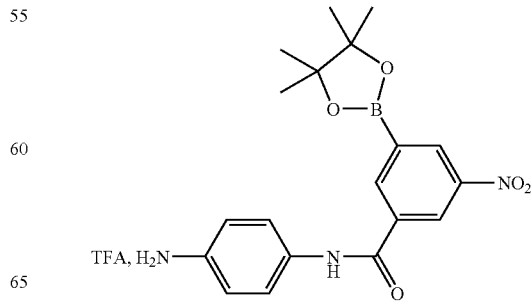

This aniline derivative was coupled to the carboxylic acid group of LysB29 in des(B30) human insulin using achromobacter lyticus protease (Morihara and Ueno, Biotech. Bioeng. 1991, 37, 693) to give 26a (yield: 4%. Mw found by ESMS: 5990 (theoretical value: 5990)). Subsequently, the ε-amino group of LysB29 was acylated selectively using γ-N-hydroxysuccinimidyl α-methyl glutamyl-$N^α$-lithocholate (U.S. Pat. No. 5,646,242) and the methyl ester group was saponified to give structure 26 (yield: 25%. Mw found by ESMS: 6478 (theoretical value: 6477)).

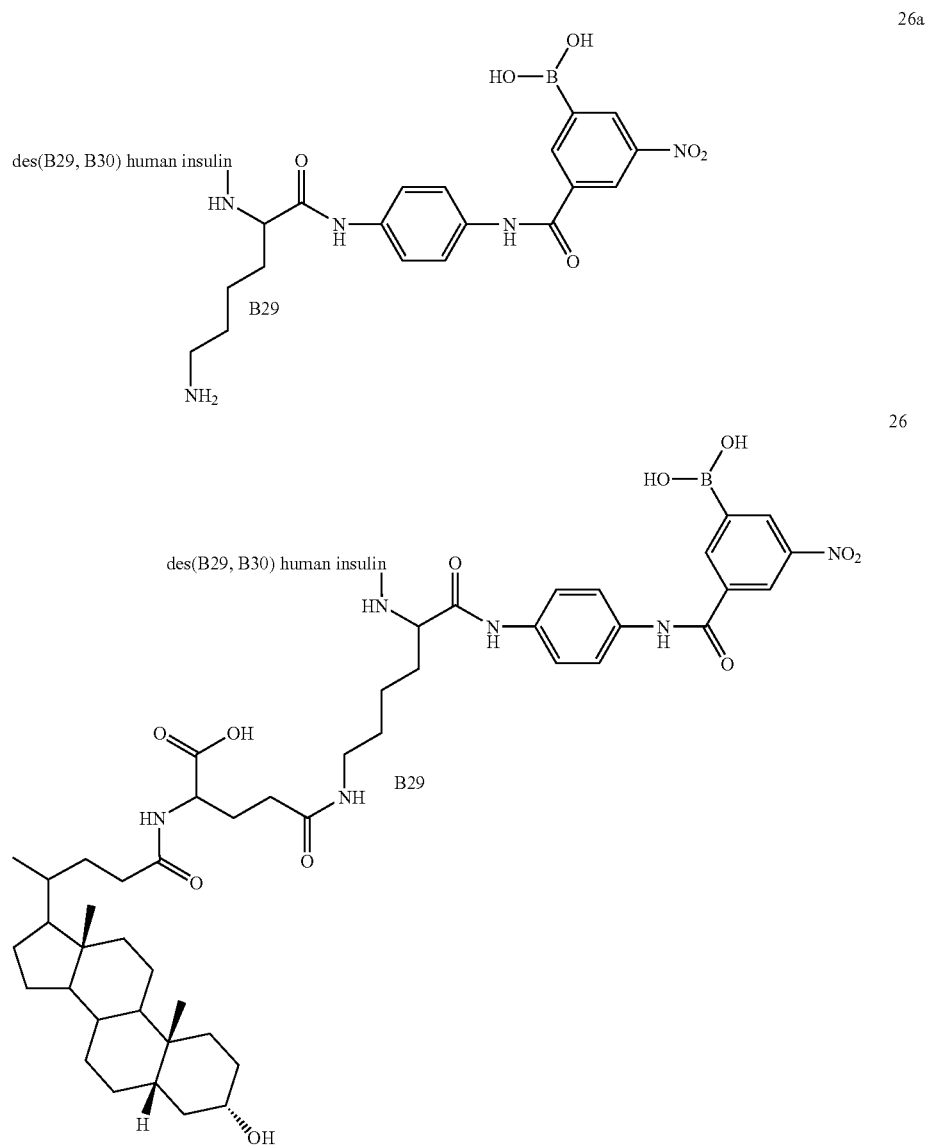

Example 27

Pro$^{B0}$-($N^α$-(2-borono-benzyl) human insulin, 27 tert-Butyl prolinate (Aldrich) was reacted with 2-(pinacolborono)benzyl bromide (Combi Blocks, CA, USA) in ether and TEA. The tert-butyl group was removed using TFA and the amino acid was treated with N-hydroxysuccinimide and DCC in THF and TEA to give N-(2-pinacolboronobenzyl), O-succinimidyl prolinate:

$^1$H-NMR (CDCl$_3$) δ: 7.69 (d, 1H, ArH), 7.41 (d, 1H, ArH), 7.34 (t, 1H, ArH), 7.20 (t, 1H, ArH), 4.07 (s, 2H, ArCH$_2$), 3.77 (m, 1H, αCH), 3.16 (m, 2H, CH$_2$N), 2.91 (m, 1H, βCH), 2.77 (s, 4H, succinyl), 2.70 (m, 1H, βCH'), 2.15 (m, 2H, CH$_2$), 1.30 (s, 12H, pinacolyl).

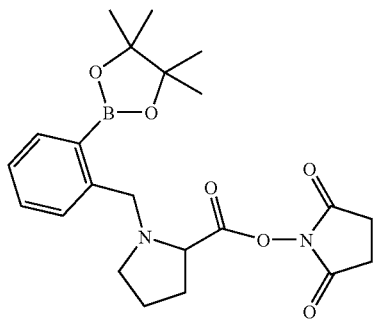

The active ester was coupled to (Gly$^{A1}$, Lys$^{B29}$-diBoc) human insulin in DMSO and the protecting groups were cleaved with TFA to give 27 (Mw found by ESMS: 6527 (theoretical value: 6526)).

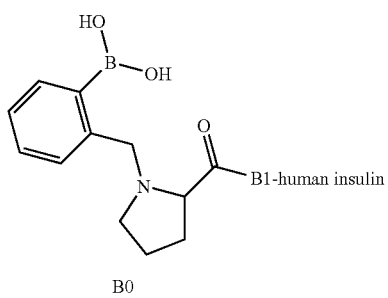

Example 28

Pro$^{B0}$-(3-nitro-5-borono-benzoyl) human insulin, 28

Pro$^{B0}$-(3-nitro-5-borono-benzoyl) human insulin, 28, was prepared by a method similar to the method used for the preparation of 27.

O-succinimidyl-3-nitro-5-pinacolborono-benzoate:

$^1$H-NMR (CDCl$_3$) δ: 9.00 (dd, 1H, ArH), 8.90 (dd, 1H, ArH), 8.83 (dd, 1H, ArH), 2.93 (s, 4H, succinyl), 1.37 (s, 12H, pinacolyl).

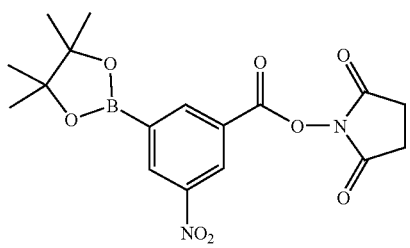

28, (yield: 51%. Mw found by ESMS: 6488 (theoretical value: 648)).

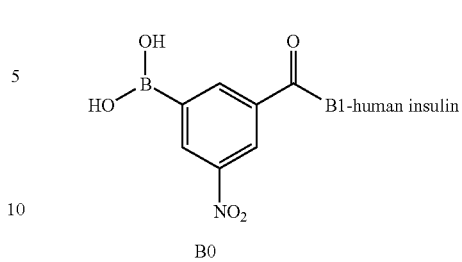

Example 29

Lys$^{B29}$(N$^ε$-(γ-glutamyl-N$^α$-lithocholoyl),Lys$^{B30}$(N$^ε$-isopropyl,N$^ε$-(2-borono)benzyl) human insulin, 29

N$^α$-tert-Butyloxycarbonyl-N$^ε$-isopropyl lysine (SennChem) was reacted with trimethylsilyldiazomethan in ethanol. The resulting methyl ester amine was reacted with 2-(pinacolborono)benzyl bromide in ether and TEA to give N$^α$-tert-butyloxycarbonyl, N$^ε$-isopropyl, N$^ε$-(2-pinacolboronobenzyl) methyl lysinate:

$^1$H-NMR (CDCl$_3$) δ: 7.68 (d, 1H, ArH), 7.57 (d, 1H, ArH), 7.34 (t, 1H, ArH), 7.18 (t, 1H, ArH), 4.94 (bd, 1H, NH), 4.23 (m, 1H, αH), 3.78 (s, 2H, ArCH$_2$), 3.70 (s, 3H, CH$_3$), 2.89 (hept, 1H, CHMe$_2$), 2.39 (m, 2H, CH$_2$N), 1.65 (m, 2H, CH$_2$), 1.53 (m, 2H, CH$_2$), 1.44 (s, 9H, Boc), 1.35 (s, 12H, pinacolyl).

Treatment with methanol and trimethylsilyl chloride, 10:1, gave N$^ε$-isopropyl, N$^ε$-(2-pinacolboronobenzyl), methyl lysinate, dihydrochloride.

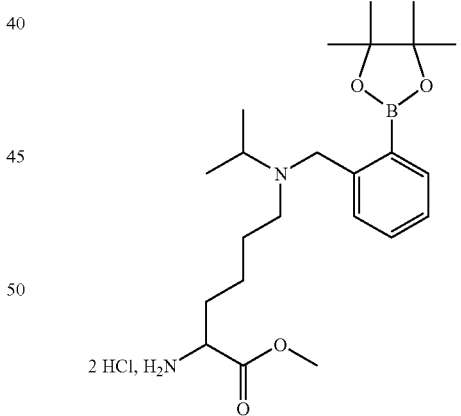

This amino acid derivative was coupled to the carboxylic acid group of LysB29 in des(B30) human insulin using achromobacter lyticus protease (Morihara and Ueno, Biotech. Bioeng. 1991, 37, 693) and the methyl ester group was saponified to give 29a (yield: 32%. Mw found by ESMS: 6011 (theoretical value: 6011)). Subsequently, the ε-amino group of LysB29 was acylated selectively using γ-N-hydroxysuccinimidyl α-methyl glutamyl-N$^α$-lithocholate (U.S. Pat. No. 5,646,242) and the Glu methyl ester group was saponified to give structure 29 (yield: 79%. Mw found by ESMS: 6498 (theoretical value: 6498)).

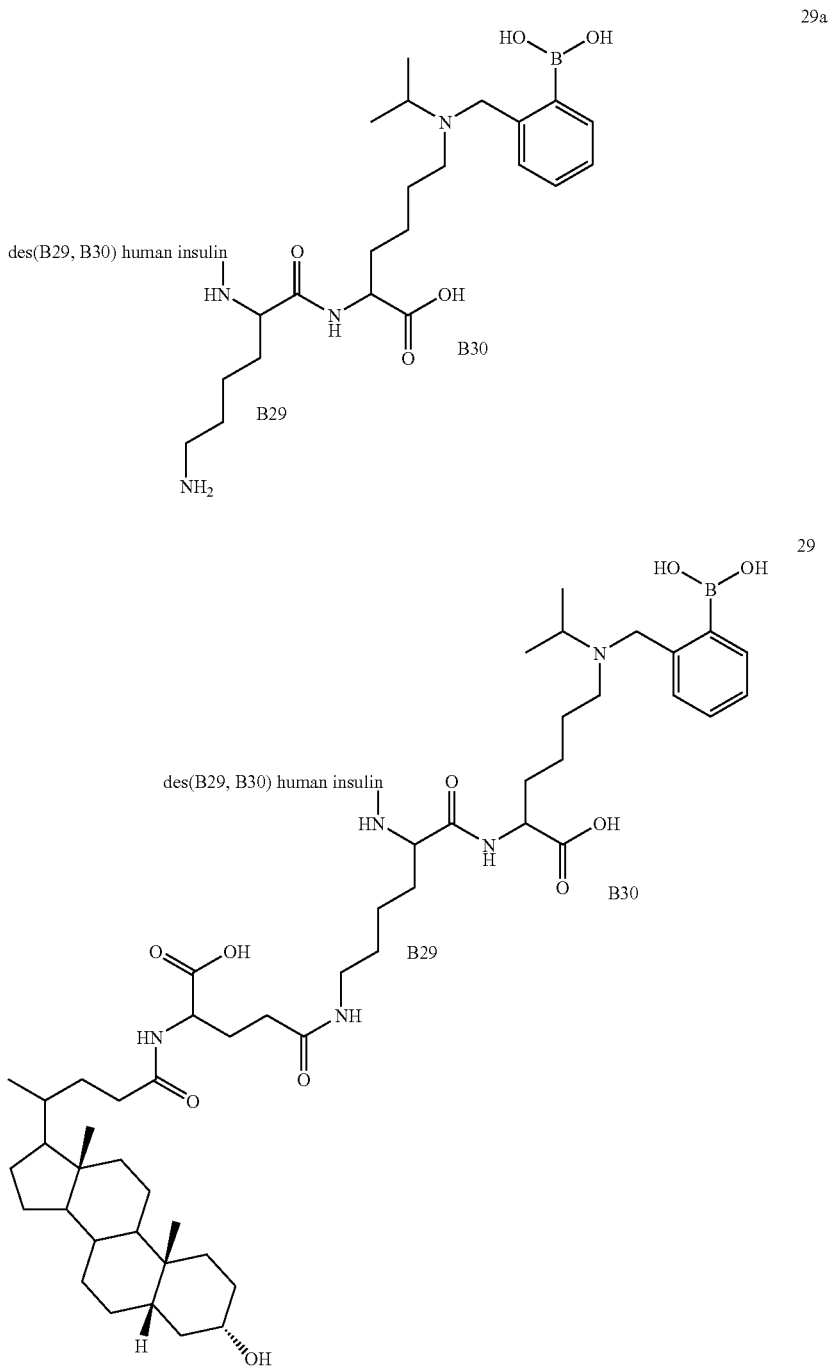

Example 30

Lys$^{B29}$($^\epsilon$N-(γ-glutamyl-N$^\alpha$-lithocholoyl),Lys$^{B30}$(N$^\epsilon$-methyl, N$^\epsilon$-(2-borono)benzyl) human insulin, 30

N$^\alpha$-tert-Butyloxycarbonyl-lysine was reacted with trimethylsilyldiazomethan in ethanol. The resulting methyl ester amine was transformed to the N$^\epsilon$-methyl derivative via benzaldehyde and sodium borohydride, formaldehyde and sodium borohydride and hydrogenolysis (Andruszkiewicz, J. Pol. Chem. 1988, 62, 257) followed by N-alkylation with 2-(pinacolborono)benzyl bromide. The resulting N$^\alpha$-tert-butyloxycarbonyl, N$^\epsilon$-methyl, N$^\epsilon$-(2-pinacolboronobenzyl) methyl lysinate was treated with methanol and trimethylsilyl chloride, 10:1, to give N$^\epsilon$-methyl, N$^\epsilon$-(2-boronobenzyl), methyl lysinate, dihydrochloride:

$^1$H-NMR δ (DMSO-d$_6$+1 dr. DCl/D$_2$O) 7.77 (d, 1H, ArH), 7.58 (d, 1H, ArH), 7.47 (m, 2H, ArH), 4.68 (d, 1H, ArCH), 4.30 (d, 1H, ArCH'), 4.03 (m, 1H, αCH), 3.78 (s, 3H, OCH$_3$), 3.11 (m, 2H, NCH$_2$), 2.62 (s, 3H, NCH$_3$), 1.88 (m, 2H, CH$_2$), 1.79 (m, 2H, CH$_2$), 1.40 (m, 2H, CH$_2$).

Mw found by LCMS: 309.2 (M+H$^+$).

51

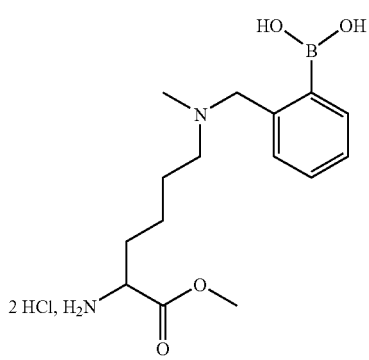

52

This amino acid derivative was coupled to the carboxylic acid group of LysB29 in des(B30) human insulin using achromobacter lyticus protease (Morihara and Ueno, Biotech. Bioeng. 1991, 37, 693) and the methyl ester group was saponified to give 30a (yield: 58%. Mw found by ESMS: 5983 (theoretical value: 5983)). Subsequently, the ε-amino group of LysB29 was acylated selectively using γ-N-hydroxysuccinimidyl α-methyl glutamyl-$N^\alpha$-lithocholate (U.S. Pat. No. 5,646,242) and the Glu methyl ester group was saponified to give structure 30 (yield: 12%. Mw found by ESMS: 6470 (theoretical value: 6470)).

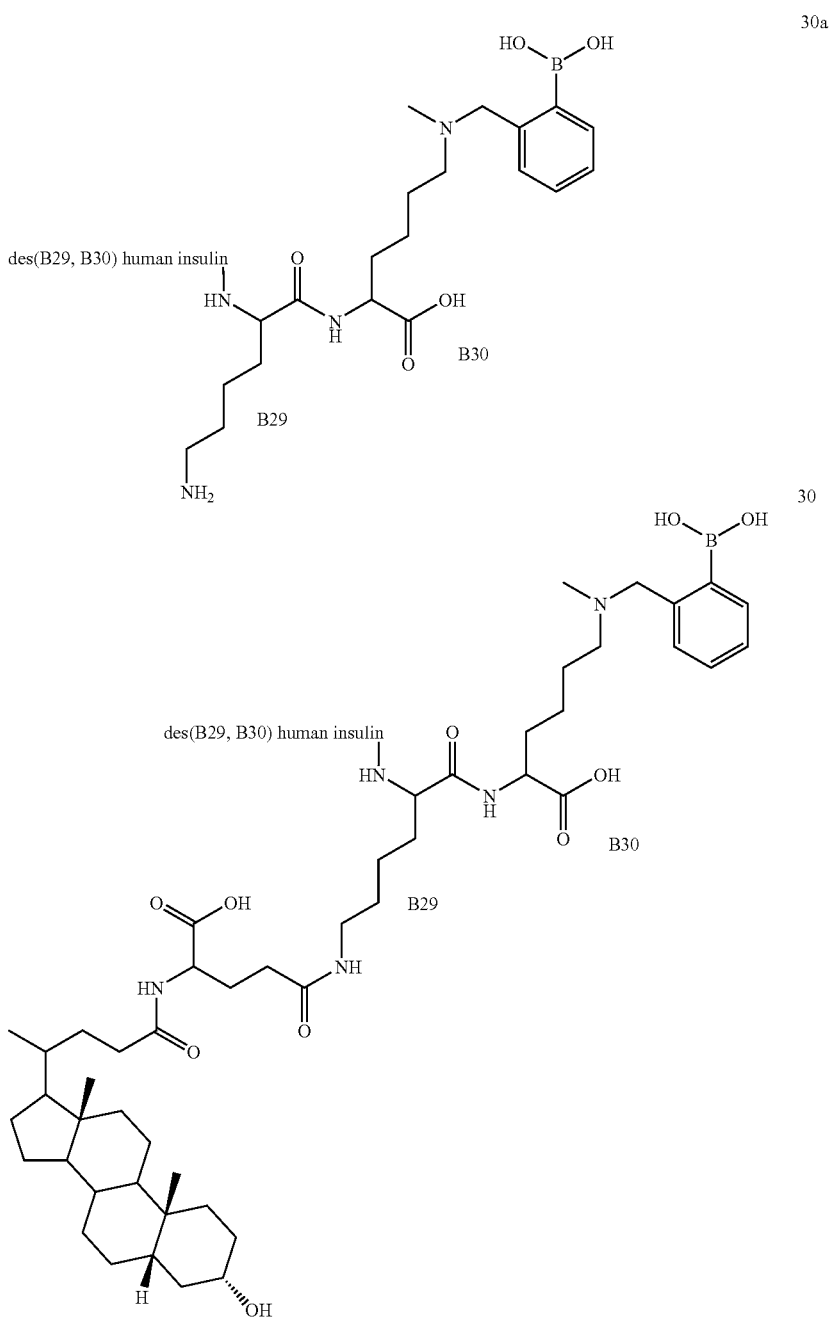

Example 31

Lys$^{B29}$(N$^\epsilon$-(γ-glutamyl-N$^\alpha$-lithocholoyl),Dab$^{B30}$(N$^\epsilon$-methyl,N$^\epsilon$-(2-borono)benzyl) human insulin, 31

The Dab$^{B30}$ analogue of 30 was prepared by a method corresponding to the method used for the preparation used for 30.

N$^\epsilon$-methyl, N$^\epsilon$-(2-boronobenzyl), methyl diaminobutyrate, dihydrochloride:

$^1$H-NMR δ (DMSO-d$_6$+1 dr. DCl/D$_2$O) 7.78 (d, 1H, ArH), 7.60 (d, 1H, ArH), 7.47 (m, 2H, ArH), 4.69 (d, 1H, ArCH), 4.36 (d, 1H, ArCH'), 4.22 (m, 1H, αCH), 3.78 (s, 3H, OCH$_3$), 3.36 (m, 2H, NCH$_2$), 2.80 (s, 3H, NCH$_3$), 2.40 (m, 2H, CH$_2$).

Mw found by LCMS: 281.0 (M+H$^+$).

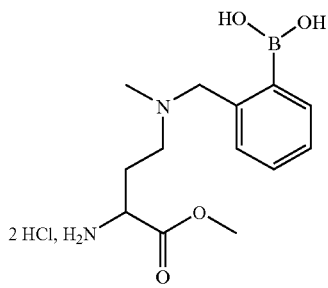

31a, (yield: 23%. Mw found by ESMS: 5955 (theoretical value: 5955)).

31, (yield: 62%. Mw found by ESMS: 6442 (theoretical value: 6442)).

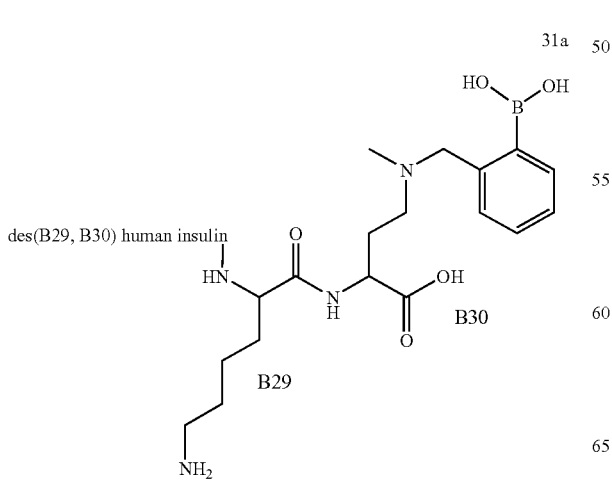

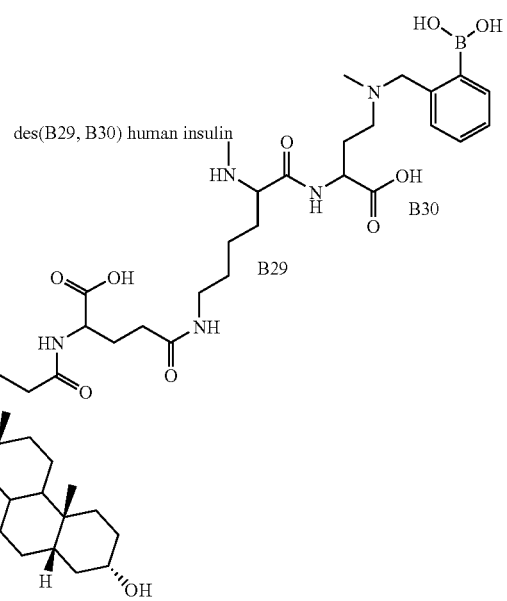

Example 32

Lys$^{B29}$(N$^\epsilon$-(γ-glutamyl-N$^\alpha$-lithocholoyl),Asp$^{B30}$(β-(N'-(2-boronobenzyl)piperazino)) human insulin, 32

N'-tert-Butyloxycarbonyl-piperazine (Aldrich) was reacted with 2-(pinacolborono)benzyl bromide in ether and TEA. The Boc-group was removed and the amine was coupled to N$^\alpha$-tert-butyloxycarbonyl α-tert-butyl aspartate using carbonyldiimidazole in DMF. The resulting aspartate was treated with TFA followed by methanol and trimethylsilyl chloride, 10:1, to give β-(N'-(2-boronobenzyl)piperazine)) methyl aspartate, dihydrochloride:

$^1$H-NMR (D$_2$O-MeOD) δ: 7.77 (d, 1H, ArH), 7.50 (m, 2H, ArH), 7.41 (t, 1H, ArH), 4.47 (s, 2H, ArCH$_2$), 4.37 (m, 1H, αCH), 3.726 (s, 3H, CH$_3$), 3.13 (m, 2H, CH$_2$).

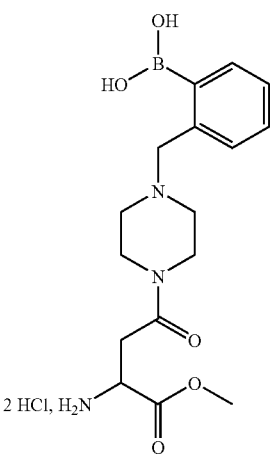

This amino acid derivative was coupled to the carboxylic acid group of LysB29 in des(B30) human insulin using achromobacter lyticus protease (Morihara and Ueno, Biotech. Bioeng. 1991, 37, 693) and the methyl ester group was saponified to give 32a (yield: 47%. Mw found by ESMS: 6025 (theoretical value: 6024)). Subsequently, the ε-amino group of LysB29 was acylated selectively using γ-N-hydroxysuccinimidyl α-methyl glutamyl-N$^\alpha$-lithocholate (U.S. Pat. No. 5,646,242) and Glu the methyl ester group was saponified to give structure 32 (yield: 50%. Mw found by ESMS: 6510 (theoretical value: 6511)).

Example 33

Lys$^{B29}$(N$^\epsilon$-(γ-glutamyl-N$^\alpha$-lithocholoyl),Glu$^{B30}$(β-(N'-(2-boronobenzyl)piperazino)) human insulin, 33

The GLU$^{B30}$ analogue of 32 was prepared by a method corresponding to the method used for the preparation used for 32.

γ-(N'-(2-boronobenzyl)piperazine)) methyl glutamate, dihydrochloride:

$^1$H-NMR (D$_2$O) δ: 7.74 (d, 1H, ArH), 7.45 (m, 2H, ArH), 7.39 (t, 1H, ArH), 4.44 (s, 2H, ArCH$_2$), 4.07 (m, 1H, αCH), 3.72 (s, 3H, CH$_3$), 2.54 (m, 2H, CH$_2$), 1.65 (m, 2H, CH$_2$), 2.13 (m, 2H, CH$_2$).

33a, (yield: 28%. Mw found by ESMS: 6039 (theoretical value: 6038)).

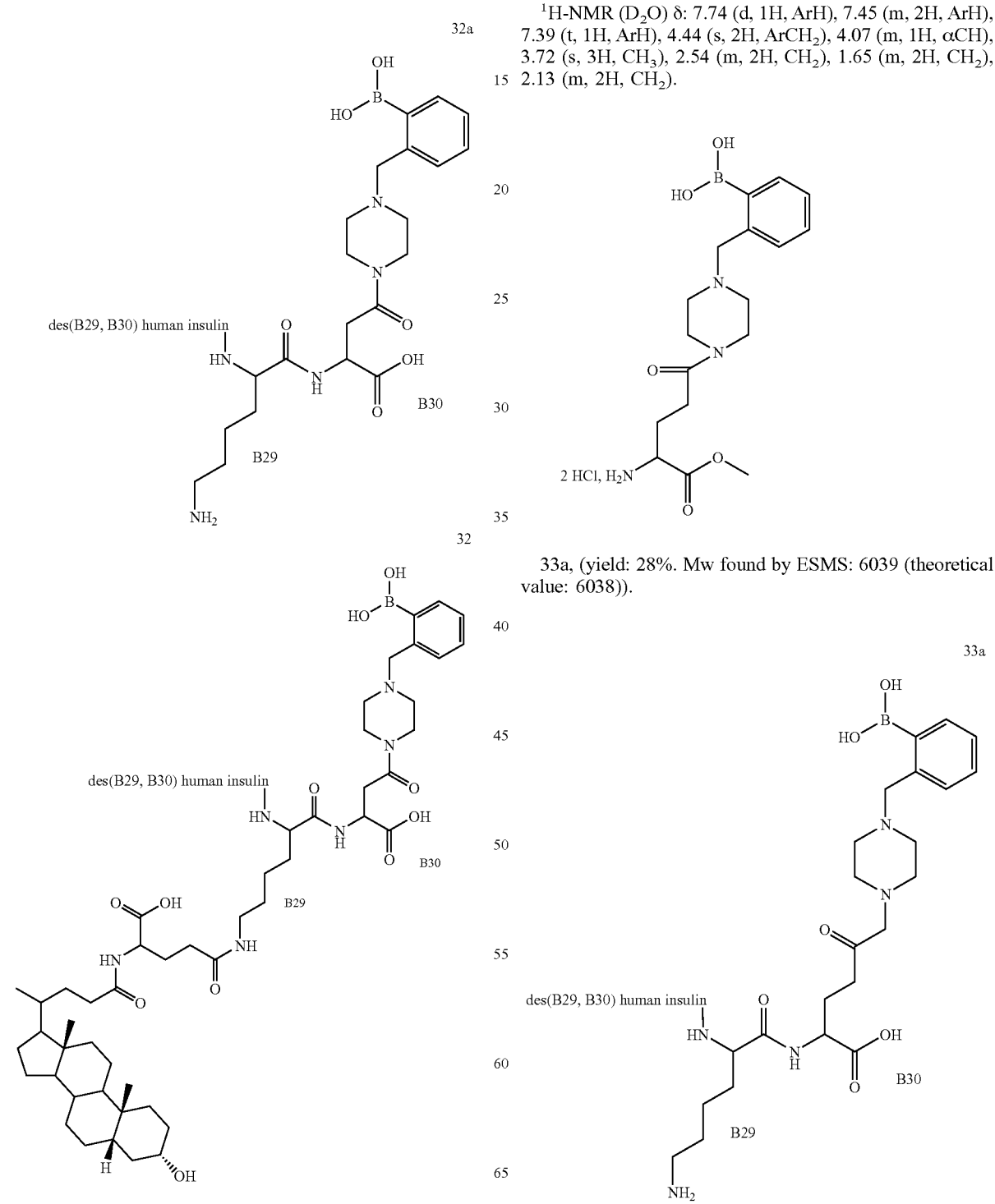

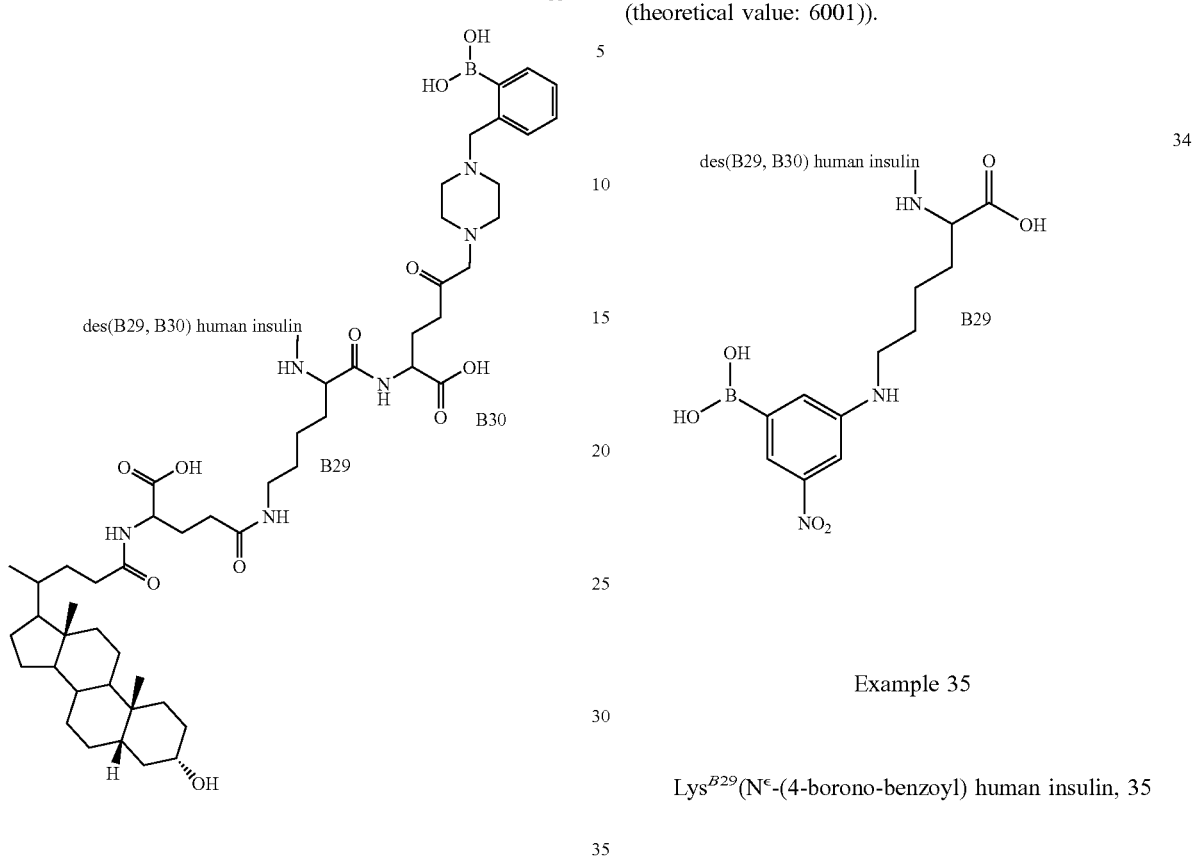

33

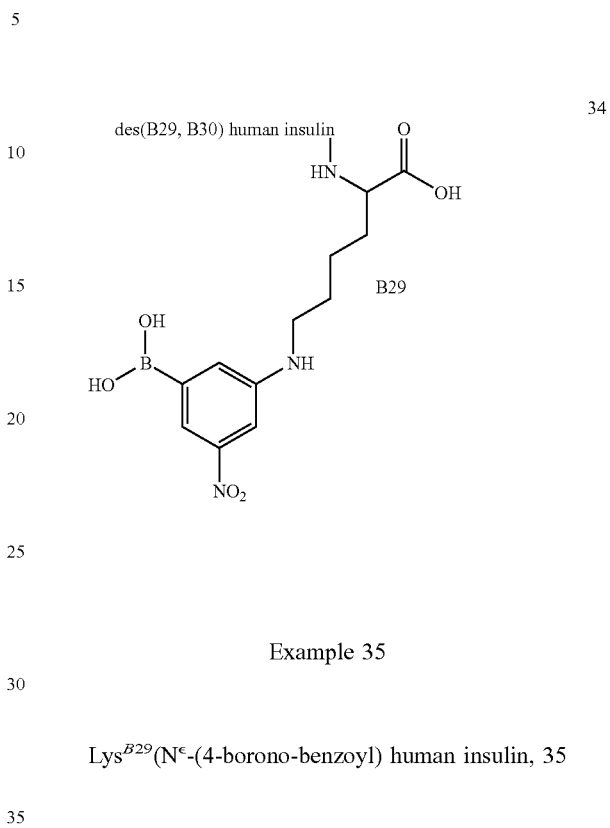

34

This material was coupled to des(B30) human insulin in acetonitrile/water to give 34 (Mw found by ESMS: 6001 (theoretical value: 6001)).

Example 34

Lys$^{B29}$-(N$^\epsilon$-(3-nitro-5-borono-benzoyl) human insulin, 34

O-Succinimidyl-3-nitro-5-pinacolborono-benzoate was made from 3-nitro-5-pinacolboronobenzoic acid and HONSu and DCC in THF.

$^1$H-NMR (CDCl$_3$) δ: 9.00 (dd, 1H, ArH), 8.90 (dd, 1H, ArH), 8.83 (dd, 1H, ArH), 2.93 (s, 4H, succinyl), 1.37 (s, 12H, pinacolyl).

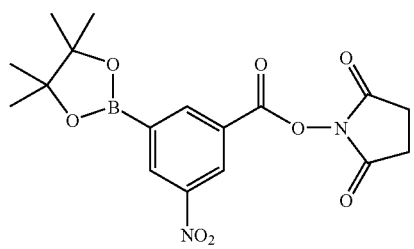

Example 35

Lys$^{B29}$(N$^\epsilon$-(4-borono-benzoyl) human insulin, 35

O-Succinimidyl-4-pinacolborono-benzoate was made from 4-pinacolborono-benzoic acid and HONSu and DCC in THF.

$^1$H-NMR (CDCl$_3$) δ: 7.68 (d, 1H, ArH), 7.57 (d, 1H, ArH), 7.34 (t, 1H, ArH), 7.18 (t, 1H, ArH), 4.94 (bd, 1H, NH), 4.23 (m, 1H, αH), 3.78 (s, 2H, ArCH$_2$), 3.70 (s, 3H, CH$_3$), 2.89 (hept, 1H, CHMe$_2$), 2.39 (m, 2H, CH$_2$N), 1.65 (m, 2H, CH$_2$), 1.53 (m, 2H, CH$_2$), 1.44 (s, 9H, Boc), 1.35 (s, 12H, pinacolyl).

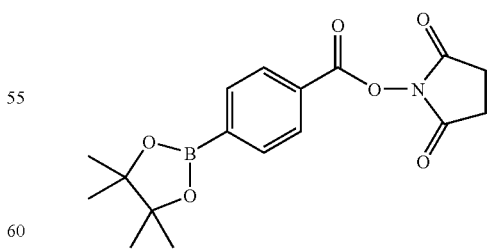

Selective acylation of the ε-amino group of LysB29 in des(B30) human insulin with O-Succinimidyl-4-pinacolborono-benzoate gave 35 (Mw found by ESMS: 5956 (theoretical value: 5855)).

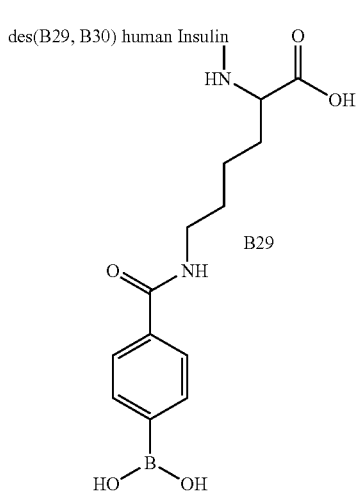

35

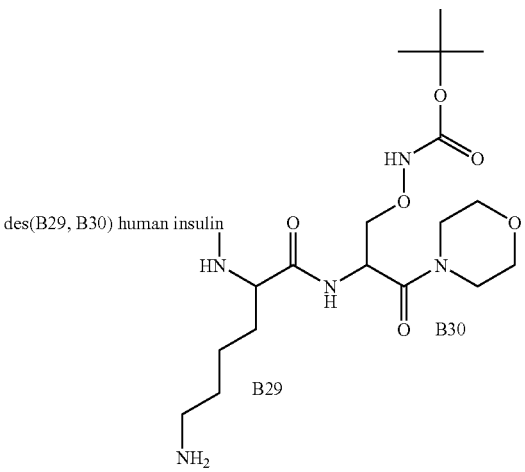

36

Example 36

B30-Ams(Boc)-morpholide human insulin, 36

Fmoc-Ams(Boc) (Speztler and Hoeg-Jensen, J. Peptide Sci. 1999, 5, 582) was coupled to morpholine using DCC in THF. The Fmoc-group was removed with LiOH in THF-water to give Ams(Boc)-morpholide.

$^1$H-NMR (CDCl$_3$) δ: 7.72 (bs, 2H, NH$_2$), 3.97 (m, 3H), 3.77 (m, 1H), 3.61 (m, 8H), 1.45 (m, 9H).

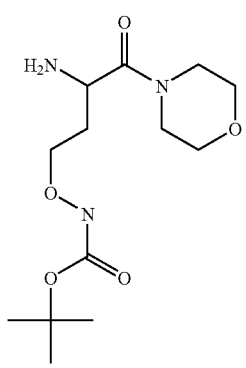

This material was coupled to the carboxylic acid group of LysB29 in des(B30) human insulin using achromobacter lyticus protease (Morihara and Ueno, Biotech. Bioeng. 1991, 37, 693) to give 36 (yield: 65%. Mw found by ESMS: 5980 (theoretical value: 5978)).

Example 37

N$^ε$-(2-boronobenzyl) methyl ornitinate, 37

N$^α$-tert-Butyloxycarbonyl-ornitine was reacted with 2-formylphenylboronic acid in methanol-triethylamine and subsequently treated with sodium borohydride (Wiskur et al, Org. Letters 2001, 3, 1311). The resulting secondary amine was transformed to the methyl ester by treatment with methanol and trimethylsilyl chloride, 10:1, to give N'-(2-boronobenzyl), methyl ornitinate, dihydrochloride.

$^1$H-NMR δ (DMSO-d$_6$) 7.69 (d, 1H, ArH), 7.56 (d, 1H, ArH), 7.41 (m, 2H, ArH), 4.28 (d, 1H, ArCH$_2$), 4.05 (m, 1H, αCH), 3.76 (s, 3H, OCH$_3$), 2.91 (m, 2H, NCH$_2$), 1.87 (m, 4H, 2CH$_2$).

Mw found by LCMS: 263.0 (M–H$_2$O+H$^+$).

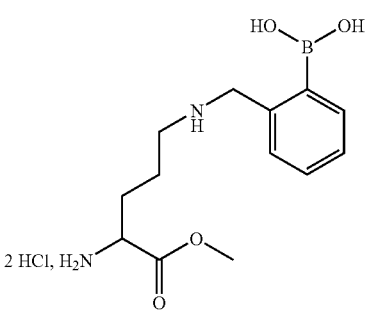

Example 38

N$^ε$-(2-boronobenzyl) methyl lysinate, 38

N$^α$-tert-Butyloxycarbonyl-lysine was reacted with 2-formylphenylboronic acid in methanol-triethylamine and subsequently treated with sodium borohydride (Wiskur et al, Org. Letters 2001, 3, 1311). The resulting secondary amine was transformed to the methyl ester by treament with methanol and trimethylsilyl chloride, 10:1, to give N$^ε$-(2-boronobenzyl), methyl lysinate, dihydrochloride.

$^1$H-NMR δ (DMSO-$d_6$) 7.79 (d, 1H, ArH), 7.53 (d, 1H, ArH), 7.40 (m, 2H, ArH), 4.46 (d, 1H, ArCH$_2$), 3.99 (m, 1H, αCH), 3.74 (s, 3H, OCH$_3$), 2.85 (m, 2H, NCH$_2$), 1.80 (m, 2H, CH$_2$), 1.67 (m, 2H, CH$_2$), 1.40 (m, 2H, CH$_2$).

Mw found by LCMS: 277.1 (M–H$_2$O+H$^+$).

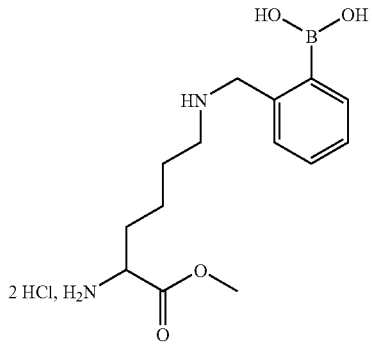

Example 39

A pharmaceutical composition comprising a solution of 600 nmol/mL of Lys$^{B29}$(N$^ε$-(γ-glutamyl-N$^α$-lithochol),Orn$^{B30}$(N-4-boronobenzenesulfonyl) human insulin, synthesized according to Example 23

4.8 mg of insulin derivative 23 was suspended in 400 μL water on an ice bath and dissolved by addition of 8 μL 1N sodium hydroxide. Further, 36 μL 0.01 M zinc acetate (corresponding to 0.5 zinc per insulin), 300 μL water, 60 μL 0.32 M phenol, 120 μL 0.16 M m-cresol, 84 μL 0.1 M sodium phosphate, 300 μL 0.5 M sodium chloride was added. Then, at room temperature, the pH value of the solution was adjusted to 7.6 by means of 7 μL 0.2 M hydrochloric acid. Finally water was added to 1.2 mL and the resulting solution was sterilized by filtration and transferred aseptically to a cartridge.

Example 40

A pharmaceutical composition comprising a solution of 600 nmol/mL of Lys$^{B29}$(N(γ-glutamyl-N$^α$-lithocholoyl),Dap$^{B30}$(N-3-nitro-5-boronobenzoyl) human insulin, synthesized according to Example 19

10 mg of insulin derivative 19 was suspended in 600 μL water on ice bath and dissolved by addition of 10 μL 1N sodium hydroxide. Further, 75 μL 0.01 M zinc acetate (corresponding to 0.5 zinc per insulin), 500 μL water, 125 μL 0.32 M phenol, 250 μL 0.16 M m-cresol, 175 μL 0.1 M sodium phosphate, 500 μL 0.5 M sodium chloride was added. Then, at room temperature, the pH value of the solution was adjusted to 7.6 by means of 10 μL 0.2 M hydrochloric acid. Finally water was added to 2.5 mL and the resulting solution was sterilized by filtration and transferred aseptically to cartridges.

Example 41

Protraction test in pigs of Lys$^{B29}$(N$^ε$-(γ-glutamyl-N$^α$-lithocholoyl),Dap$^{B30}$(N$^ε$-3-nitro-5-boronobenzoyl) human insulin, synthesized according to Example 19

A formulation was prepared according to Example 40 and Tyr($^{125}$I)$^{A14}$ tracer was added just after dissolution of insulin derivative 19. 100 μL of the formulation was injected subcutaneously in one side of the neck with a reference formulation in the other side of the neck in 5 pigs and disappearance from the depots measured by external γ-counters. The T$_{50\%}$ was 13.4 h for the insulin derivative 19 and 9.2 h for the reference compound, N$^{εB29}$ myristoyl des(B30) human insulin (Ribel, U. et al., The Pig as a Model for Subcutaneous Absorption in Man. In: M. Serrano-Rios and P. J. Lefebre (Eds.): Diabetes 1985; Proceedings of the 12$^{th}$ Congress of the International Diabetes Federation, Madrid, Spain, 1985 (Excerpta Medica, Amsterdam, (1986, 891–896)) (Havelund, S et el., Acylated Insulin, WO 95/07931 (Novo Nordisk)).

The invention claimed is:

1. A crystalline, or soluble aggregate or aggregate-forming insulin derivative, wherein the insulin derivative comprises a lipophilic substituent, and a glucose-sensing group, wherein the glucose-sensing group is an aryl boronate group, wherein the glucose-sensing group is built into a substituent capable of effecting the formation of high molecular aggregates, and wherein the substituent causing aggregation is a lipophilic group.

2. The insulin derivative of claim 1, wherein the insulin derivative is a natural insulin or an insulin analogue.

3. The insulin derivative of claim 1, having a glucose affinity in the range of 0.01 µM to 10 mM.

4. The insulin derivative of claim 1, wherein the aryl boronate group comprises an electron-withdrawing substituent.

5. The insulin derivative of claim 4, wherein the electron-withdrawing substituent is selected from the group consisting of sulfo, carboxy, nitro, cyano and fluoro.

6. The insulin derivative of claim 4, which has an amino group in proximity to the boronate moiety in the form of a 2-aminomethylarylboronate.

7. The insulin derivative of claim 6, which has an amino group within 2.0 Ångstrom from the boron atom.

8. The insulin derivative of claim 1, wherein the arylboronate group is selected among the following groups, wherein R designates the insulin moiety including a lipophilic substituent and an optional linker, and R' designates hydrogen, methyl, ethyl, propyl, isopropyl or benzyl:

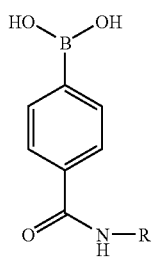
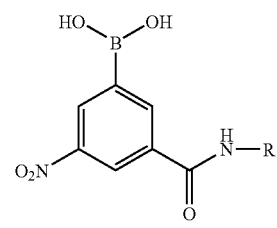
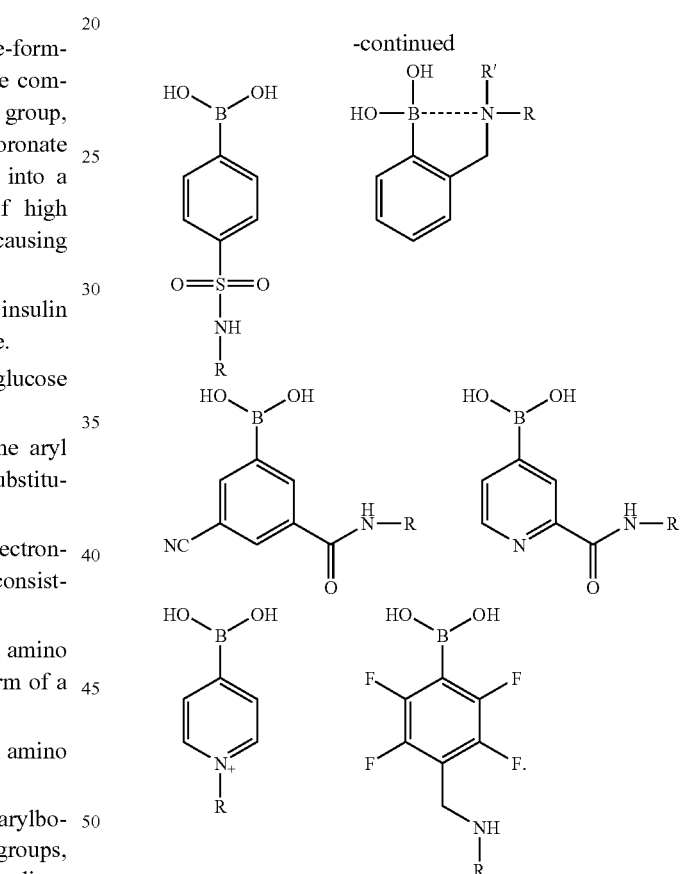

9. The insulin derivative of claim 1, wherein the arylboronate group is attached to the insulin moiety via the α-amino group of GlyA1 or PheB1, or via the ε-amino group of a Lys residue at position B3, B28, B29 or B30 or an Orn residue, a Dap residue, a Dab residue, an Asp residue or a Glu residue at position B30.

10. The insulin derivative of claim 1, wherein the arylboronate group is attached to the insulin moiety via a linker.

11. The insulin derivative of claim 10, wherein the linker is selected from the group consisting of γ-glutamyl, α-glutamyl, β-aspartyl, α-aspartyl, β-alanine, piperazine and aniline.

12. The insulin derivative of claim 1, wherein the glucose sensing aryl boronate is a part of the amino acid residue in position B26 of the insulin moiety.

13. An insulin derivative comprising a glucose-sensing group, wherein the glucose sensing group is a peptide or pseudopeptide, optionally comprising Asn, Trp, His, Asp, Arg or a boronate containing amino acid.

14. The insulin derivative of claim 13, wherein the glucose sensing peptide is comprised within the residues 26–30 of the B-chain, optionally extended beyond the C-terminal residue 30 of the B-chain.

15. The insulin derivative of claim 1, wherein the lipophilic group is a derivative of a bile acid selected from the group comprising lithocholic acid, hyocholic acid, hyodeoxycholic acid and chenodeoxycholic acid.

16. The insulin derivative of claim 15, wherein the lipophilic group is attached to the insulin moiety via a γ-glutamyl, α-glutamyl, β-aspartyl, α-aspartyl or β-alanine spacer.

17. The insulin derivative of claim 1, wherein the lipophilic group is a derivative of an α,ω-dicarboxylic acid having from 10 to 30 carbon atoms.

18. An insulin derivative according to claim 1 comprising a monosaccharide, disaccharide, or trisaccaride group, capable of binding to an insulin derivative having a glucose-sensing group.

19. The insulin derivative of claim 1, further comprising a monosaccharide, disaccharide, or trisaccaride substitution.

20. The insulin derivative of claim 1, capable of forming water soluble, high molecular aggregates having a molecular weight >150 kDa.

21. A water soluble, protracted, glucose dependent pharmaceutical composition comprising one or more of the insulin derivatives of claim 1.

22. A soluble, biphasic-acting insulin preparation comprising one or more of the insulin derivatives of claim 1, mixed with human insulin or an insulin with rapid onset of action, such as human insulin or des(B30) human insulin or Asp$^{B28}$ human insulin or Lys$^{B28}$Pro$^{B29}$ human insulin or Gly$^{A21}$,Lys$^{B3}$,Ile$^{B28}$ human insulin, or Asp$^{A21}$,Lys$^{B3}$,Ile$^{B28}$ human insulin in ratios from 10:1 to 1:10.

23. A soluble insulin preparation comprising an insulin derivative according to claim 1, characterized by having a rate of absorption from an injected depot, which rate is of absorption increases as the glucose concentration in the tissue increases, and decreases as the glucose concentration decreases.

24. Crystalline preparations of one or more of the insulin derivatives of claim 1.

25. A method of treating diabetes in a patient in need of such a treatment, comprising administering to the patient a therapeutically effective amount of the insulin derivative of claim 1.

26. A method of treating diabetes in a patient in need of such a treatment, comprising administering to the patient a therapeutically effective amount of the insulin derivative of claim 13.

* * * * *

SEQUENCE LISTING

```
<160> NUMBER OF SEQ ID NOS: 18

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
```

-continued

```
<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 5
<211> LENGTH: 21
<212> TYPE: PRT
<213> ORGANISM: Homo sapiens

<400> SEQUENCE: 5

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 6
<211> LENGTH: 30
<212> TYPE: PRT
<213> ORGANISM: Homo sapiens

<400> SEQUENCE: 6

Phe Val Lys Gln His Leu Cys Gly Ser His Leu Val Glu Ala Leu Tyr
1               5                   10                  15

Leu Val Cys Gly Glu Arg Gly Phe Phe Tyr Thr Ile Lys Thr
            20                  25                  30

<210> SEQ ID NO 7
<211> LENGTH: 21
<212> TYPE: PRT
<213> ORGANISM: Homo sapiens

<400> SEQUENCE: 7

Gly Ile Val Glu Gln Cys Cys Thr Ser Ile Cys Ser Leu Tyr Gln Leu
1               5                   10                  15

Glu Asn Tyr Cys Asp
            20
```

```
<210> SEQ ID NO 8
<211> LENGTH: 29
<212> TYPE: PRT
<213> ORGANISM: Homo sapiens

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 9
<211> LENGTH: 30
<212> TYPE: PRT
<213> ORGANISM: Homo sapiens

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Phe Thr Pro Lys Thr
            20                  25                  30

<210> SEQ ID NO 10
<211> LENGTH: 30
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: x = ornithine

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Xaa
            20                  25                  30

<210> SEQ ID NO 11
<211> LENGTH: 30
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: x = diaminopropionic acid

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Xaa
            20                  25                  30

<210> SEQ ID NO 12
<211> LENGTH: 30
<212> TYPE: PRT
<213> ORGANISM: Homo sapiens

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Lys
            20                  25                  30
```

```
<210> SEQ ID NO 13
<211> LENGTH: 31
<212> TYPE: PRT
<213> ORGANISM: Homo sapiens

<400> SEQUENCE: 13

Pro Phe Val Asn Gln His Leu Cys Gly Ser His Leu Val Glu Ala Leu
1               5                   10                  15

Tyr Leu Val Cys Gly Glu Arg Gly Phe Phe Tyr Thr Pro Lys Thr
            20                  25                  30

<210> SEQ ID NO 14
<211> LENGTH: 30
<212> TYPE: PRT
<213> ORGANISM: Homo sapiens

<400> SEQUENCE: 14

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Asp
            20                  25                  30

<210> SEQ ID NO 15
<211> LENGTH: 30
<212> TYPE: PRT
<213> ORGANISM: Homo sapiens

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Glu
            20                  25                  30

<210> SEQ ID NO 16
<211> LENGTH: 30
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: x = O-aminoserine(BOC)

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Xaa
            20                  25                  30

<210> SEQ ID NO 17
<211> LENGTH: 30
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: x = diaminobutyric acid

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Xaa
            20                  25                  30
```

```
<210> SEQ ID NO 18
<211> LENGTH: 7
<212> TYPE: PRT
<213> ORGANISM: homo sapien
<220> FEATURE:
<221> NAME/KEY: MISC_FEATURE
<222> LOCATION: (4)..(4)
<223> OTHER INFORMATION: Xaa=NBPhe
<220> FEATURE:
<221> NAME/KEY: MISC_FEATURE
<222> LOCATION: (7)..(7)
<223> OTHER INFORMATION: Xaa=Lys(lithocholoyl)

<400> SEQUENCE: 18

Gly Phe Phe Xaa Thr Pro Xaa
1               5
```